(12) United States Patent
Batch et al.

(10) Patent No.: US 10,668,211 B2
(45) Date of Patent: Jun. 2, 2020

(54) MANAGEMENT OF PENDING MEDICATION ORDERS

(71) Applicant: CAREFUSION 303, INC., San Diego, CA (US)

(72) Inventors: Richard M. Batch, Del Mar, CA (US); Timothy W. Vanderveen, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 29 days.

(21) Appl. No.: 15/990,526

(22) Filed: May 25, 2018

(65) Prior Publication Data

US 2018/0272061 A1     Sep. 27, 2018

Related U.S. Application Data

(63) Continuation of application No. 14/848,063, filed on Sep. 8, 2015, now Pat. No. 9,981,085, which is a
(Continued)

(51) Int. Cl.
    *A61M 5/168*      (2006.01)
    *G06Q 50/24*      (2012.01)
    (Continued)

(52) U.S. Cl.
    CPC ........ *A61M 5/16827* (2013.01); *A61M 5/172* (2013.01); *G06F 19/00* (2013.01);
    (Continued)

(58) Field of Classification Search
    CPC .............. A61M 5/16827; A61M 5/172; A61M 2205/3569; G16H 20/17; G06F 19/3468
See application file for complete search history.

(56) References Cited

U.S. PATENT DOCUMENTS 2,141,006 A    12/1938   Marinsky
3,724,455 A    4/1973   Unger
(Continued)

FOREIGN PATENT DOCUMENTS

CA      2472098 A1    7/2003
CA      2554903 A1    4/2005
(Continued)

OTHER PUBLICATIONS

Australian Office Action for Application No. 2014268828, dated Jul. 26, 2019, 4 pages.
(Continued)

*Primary Examiner* — Bradley J Osinski
(74) *Attorney, Agent, or Firm* — Morgan, Lewis & Bockius LLP

(57) ABSTRACT

Pending medication orders are presented on the controller of an infusion pump to which a patient has been identified. All pending medication orders are displayed on the screen of the controller and any may be selected by the clinician. Selecting a pending order at the controller that involves an infusion to the patient also results in automatic programming of the infusion pump in accordance with that order. Selection of an oral medication at the controller results, as does selection of any other order, in notification to the healthcare facility server that the order is being administered. Such notification resolves open controlled item transactions as well as provides information that may be relevant to a patient's EMAR. Selection of a pending order may occur manually or automatically through identification of a medication.

20 Claims, 6 Drawing Sheets

Related U.S. Application Data continuation of application No. 11/326,145, filed on Dec. 30, 2005, now Pat. No. 9,427,520.

(60) Provisional application No. 60/652,382, filed on Feb. 11, 2005.

(51) Int. Cl.
*G06F 19/00* (2018.01)
*A61M 5/172* (2006.01)
*G16H 20/17* (2018.01)
*G16H 10/60* (2018.01)

(52) U.S. Cl.
CPC ......... *G06F 19/3468* (2013.01); *G06Q 50/24* (2013.01); *G16H 10/60* (2018.01); *G16H 20/17* (2018.01); *A61M 2205/3561* (2013.01); *A61M 2205/3569* (2013.01); *A61M 2205/6072* (2013.01)

(56) References Cited

U.S. PATENT DOCUMENTS

| | | |
|---|---|---|
| 3,831,006 A | 8/1974 | Chaffin, III et al. |
| 3,848,112 A | 11/1974 | Weichselbaum et al. |
| 3,872,448 A | 3/1975 | Mitchell, Jr. |
| 3,898,984 A | 8/1975 | Mandel et al. |
| 3,910,260 A | 10/1975 | Sarnoff et al. |
| 3,921,196 A | 11/1975 | Patterson |
| 3,970,996 A | 7/1976 | Yasaka et al. |
| 4,051,522 A | 9/1977 | Healy et al. |
| 4,135,241 A | 1/1979 | Stanis et al. |
| 4,164,320 A | 8/1979 | Irazoqui et al. |
| 4,216,462 A | 8/1980 | McGrath et al. |
| 4,237,344 A | 12/1980 | Moore |
| 4,315,309 A | 2/1982 | Coli |
| 4,321,461 A | 3/1982 | Walter, Jr. et al. |
| 4,360,125 A | 11/1982 | Martindale et al. |
| 4,373,527 A | 2/1983 | Fischell |
| 4,476,381 A | 10/1984 | Rubin |
| 4,604,847 A | 8/1986 | Moulding, Jr. et al. |
| 4,636,950 A | 1/1987 | Caswell et al. |
| 4,674,652 A | 6/1987 | Aten et al. |
| 4,676,776 A | 6/1987 | Howson |
| 4,688,026 A | 8/1987 | Scribner et al. |
| 4,695,954 A | 9/1987 | Rose et al. |
| 4,696,671 A | 9/1987 | Epstein et al. |
| 4,731,726 A | 3/1988 | Allen, III |
| 4,733,364 A | 3/1988 | Yamagata |
| 4,756,706 A | 7/1988 | Kerns et al. |
| 4,785,969 A | 11/1988 | McLaughlin |
| 4,788,449 A | 11/1988 | Katz |
| 4,803,625 A | 2/1989 | Fu et al. |
| 4,810,243 A | 3/1989 | Howson |
| 4,828,545 A | 5/1989 | Epstein et al. |
| 4,831,562 A | 5/1989 | McIntosh et al. |
| 4,835,372 A | 5/1989 | Gombrich et al. |
| 4,839,806 A | 6/1989 | Goldfischer et al. |
| 4,847,764 A | 7/1989 | Halvorson |
| 4,850,009 A | 7/1989 | Zook et al. |
| 4,853,521 A | 8/1989 | Claeys et al. |
| 4,855,909 A | 8/1989 | Vincent et al. |
| 4,857,713 A | 8/1989 | Brown |
| 4,857,716 A | 8/1989 | Gombrich et al. |
| 4,865,584 A | 9/1989 | Epstein et al. |
| 4,882,575 A | 11/1989 | Kawahara |
| 4,899,839 A | 2/1990 | Dessertine et al. |
| 4,916,441 A | 4/1990 | Gombrich |
| 4,918,604 A | 4/1990 | Baum |
| 4,925,444 A | 5/1990 | Orkin et al. |
| 4,942,544 A | 7/1990 | McIntosh et al. |
| 4,950,246 A | 8/1990 | Muller |
| 4,967,928 A | 11/1990 | Carter |
| 4,970,669 A | 11/1990 | McIntosh et al. |
| 4,978,335 A | 12/1990 | Arthur, III |
| 5,001,630 A | 3/1991 | Wiltfong |
| 5,006,699 A | 4/1991 | Felkner et al. |
| 5,036,462 A | 7/1991 | Kaufman et al. |
| 5,036,852 A | 8/1991 | Leishman |
| 5,072,383 A | 12/1991 | Brimm et al. |
| 5,077,666 A | 12/1991 | Brimm et al. |
| 5,078,683 A | 1/1992 | Sancoff et al. |
| 5,088,056 A | 2/1992 | McIntosh et al. |
| 5,088,981 A | 2/1992 | Howson et al. |
| 5,100,380 A | 3/1992 | Epstein et al. |
| 5,126,957 A | 6/1992 | Kaufman et al. |
| 5,142,484 A | 8/1992 | Kaufman et al. |
| 5,153,416 A | 10/1992 | Neeley |
| 5,153,827 A | 10/1992 | Coutre et al. |
| 5,164,575 A | 11/1992 | Neeley et al. |
| 5,166,498 A | 11/1992 | Neeley |
| 5,171,977 A | 12/1992 | Morrison |
| 5,181,910 A | 1/1993 | Scanlon |
| 5,207,642 A | 5/1993 | Orkin et al. |
| 5,235,507 A | 8/1993 | Sackler et al. |
| 5,256,157 A | 10/1993 | Samiotes et al. |
| 5,258,906 A | 11/1993 | Kroll et al. |
| 5,265,010 A | 11/1993 | Evans-Paganelli et al. |
| 5,267,174 A | 11/1993 | Kaufman et al. |
| 5,291,399 A | 3/1994 | Chaco |
| 5,292,029 A | 3/1994 | Pearson |
| 5,307,263 A | 4/1994 | Brown |
| 5,312,334 A | 5/1994 | Nara et al. |
| 5,314,243 A | 5/1994 | McDonald et al. |
| 5,315,505 A | 5/1994 | Pratt et al. |
| 5,317,506 A | 5/1994 | Coutre et al. |
| H1324 H | 6/1994 | Dalke et al. |
| 5,331,547 A | 7/1994 | Laszlo |
| 5,356,378 A | 10/1994 | Doan |
| 5,367,555 A | 11/1994 | Isoyama |
| 5,368,554 A | 11/1994 | Nazarian et al. |
| 5,371,692 A | 12/1994 | Draeger et al. |
| 5,374,813 A | 12/1994 | Shipp |
| 5,376,070 A | 12/1994 | Purvis et al. |
| 5,378,231 A | 1/1995 | Johnson et al. |
| 5,382,232 A | 1/1995 | Hague et al. |
| 5,390,238 A | 2/1995 | Kirk et al. |
| 5,401,059 A | 3/1995 | Ferrario |
| 5,404,384 A | 4/1995 | Colburn et al. |
| 5,408,443 A | 4/1995 | Weinberger |
| 5,412,372 A | 5/1995 | Parkhurst et al. |
| 5,412,564 A | 5/1995 | Ecer |
| 5,416,695 A | 5/1995 | Stutman et al. |
| 5,456,691 A | 10/1995 | Snell |
| 5,460,605 A | 10/1995 | Tuttle et al. |
| 5,465,082 A | 11/1995 | Chaco |
| 5,472,614 A | 12/1995 | Rossi |
| 5,502,944 A | 4/1996 | Kraft et al. |
| 5,515,426 A | 5/1996 | Yacenda et al. |
| 5,522,798 A | 6/1996 | Johnson et al. |
| 5,533,079 A | 7/1996 | Colburn et al. |
| 5,536,084 A | 7/1996 | Curtis et al. |
| 5,538,006 A | 7/1996 | Heim et al. |
| 5,542,420 A | 8/1996 | Goldman et al. |
| 5,544,649 A | 8/1996 | David et al. |
| 5,544,661 A | 8/1996 | Davis et al. |
| 5,547,470 A | 8/1996 | Johnson et al. |
| 5,561,412 A | 10/1996 | Novak et al. |
| 5,562,232 A | 10/1996 | Pearson |
| 5,564,803 A | 10/1996 | McDonald et al. |
| 5,573,506 A | 11/1996 | Vasko |
| 5,582,593 A | 12/1996 | Hultman |
| 5,583,758 A | 12/1996 | McIlroy et al. |
| 5,592,374 A | 1/1997 | Fellegara et al. |
| 5,594,786 A | 1/1997 | Chaco et al. |
| 5,597,995 A | 1/1997 | Williams et al. |
| 5,601,445 A | 2/1997 | Schipper et al. |
| 5,622,429 A | 4/1997 | Heinze |
| 5,628,309 A | 5/1997 | Brown |
| 5,630,710 A | 5/1997 | Tune et al. |
| 5,633,910 A | 5/1997 | Cohen |
| 5,643,212 A | 7/1997 | Coutre et al. |
| 5,644,778 A | 7/1997 | Burks et al. |
| 5,645,531 A | 7/1997 | Thompson et al. |

(56) References Cited

U.S. PATENT DOCUMENTS

| | | |
|---|---|---|
| 5,651,775 A | 7/1997 | Walker et al. |
| 5,655,118 A | 8/1997 | Heindel et al. |
| 5,657,236 A | 8/1997 | Conkright |
| 5,658,250 A | 8/1997 | Blomquist et al. |
| 5,672,154 A | 9/1997 | Sillen et al. |
| 5,681,285 A | 10/1997 | Ford et al. |
| 5,683,367 A | 11/1997 | Jordan et al. |
| 5,685,844 A | 11/1997 | Marttila |
| 5,689,229 A | 11/1997 | Chaco et al. |
| 5,692,640 A | 12/1997 | Caulfield et al. |
| 5,699,038 A | 12/1997 | Ulrich et al. |
| 5,700,998 A | 12/1997 | Palti |
| 5,703,786 A | 12/1997 | Conkright |
| 5,704,352 A | 1/1998 | Tremblay et al. |
| 5,710,551 A | 1/1998 | Ridgeway |
| 5,712,913 A | 1/1998 | Chaum |
| 5,713,856 A | 2/1998 | Eggers et al. |
| 5,721,913 A | 2/1998 | Ackroff et al. |
| 5,733,259 A | 3/1998 | Valcke et al. |
| 5,737,539 A | 4/1998 | Edelson et al. |
| 5,738,102 A | 4/1998 | Lemelson |
| 5,752,235 A | 5/1998 | Kehr et al. |
| 5,758,095 A | 5/1998 | Albaum et al. |
| 5,758,096 A | 5/1998 | Barsky et al. |
| 5,760,704 A | 6/1998 | Barton et al. |
| 5,764,034 A | 6/1998 | Bowman et al. |
| 5,772,585 A | 6/1998 | Lavin et al. |
| 5,774,865 A | 6/1998 | Glynn |
| 5,781,442 A | 7/1998 | Engleson et al. |
| 5,790,409 A | 8/1998 | Fedor et al. |
| 5,795,327 A | 8/1998 | Wilson et al. |
| 5,803,906 A | 9/1998 | Pratt et al. |
| 5,807,321 A | 9/1998 | Stoker et al. |
| 5,807,336 A | 9/1998 | Russo et al. |
| 5,819,229 A | 10/1998 | Boppe |
| 5,822,418 A | 10/1998 | Yacenda et al. |
| 5,822,544 A | 10/1998 | Chaco et al. |
| 5,832,488 A | 11/1998 | Eberhardt |
| 5,833,599 A | 11/1998 | Schrier et al. |
| 5,842,173 A | 11/1998 | Strum et al. |
| 5,842,976 A | 12/1998 | Williamson |
| 5,845,253 A | 12/1998 | Rensimer et al. |
| 5,845,254 A | 12/1998 | Lockwood et al. |
| 5,845,255 A | 12/1998 | Mayaud |
| 5,845,264 A | 12/1998 | Nellhaus |
| 5,848,593 A | 12/1998 | McGrady et al. |
| 5,850,344 A | 12/1998 | Conkright |
| 5,852,408 A | 12/1998 | Christiansen et al. |
| 5,855,550 A | 1/1999 | Lai et al. |
| 5,867,821 A | 2/1999 | Ballantyne et al. |
| 5,871,465 A | 2/1999 | Vasko |
| 5,883,806 A | 3/1999 | Meador et al. |
| 5,885,245 A | 3/1999 | Lynch et al. |
| 5,894,273 A | 4/1999 | Meador et al. |
| 5,895,371 A | 4/1999 | Levitas et al. |
| 5,899,998 A | 5/1999 | McGauley et al. |
| 5,903,211 A | 5/1999 | Flego et al. |
| 5,905,653 A | 5/1999 | Higham et al. |
| 5,907,490 A | 5/1999 | Oliver |
| 5,911,132 A | 6/1999 | Sloane |
| 5,911,687 A | 6/1999 | Sato et al. |
| 5,912,818 A | 6/1999 | McGrady et al. |
| 5,920,054 A | 7/1999 | Uber, III |
| 5,920,263 A | 7/1999 | Huttenhoff et al. |
| 5,928,329 A | 7/1999 | Clark et al. |
| 5,930,145 A | 7/1999 | Yuyama et al. |
| 5,935,099 A | 8/1999 | Peterson et al. |
| 5,941,710 A | 8/1999 | Lampotang et al. |
| 5,942,986 A | 8/1999 | Shabot et al. |
| 5,950,630 A | 9/1999 | Portwood et al. |
| 5,950,632 A | 9/1999 | Reber et al. |
| 5,953,099 A | 9/1999 | Walach |
| 5,954,641 A | 9/1999 | Kehr et al. |
| 5,957,885 A | 9/1999 | Bollish et al. |
| 5,961,036 A | 10/1999 | Michael et al. |
| 5,961,446 A | 10/1999 | Beller et al. |
| 5,971,593 A | 10/1999 | McGrady |
| 5,985,371 A | 11/1999 | Fujioka et al. |
| 5,995,077 A | 11/1999 | Wilcox et al. |
| 6,000,828 A | 12/1999 | Leet |
| 6,003,006 A | 12/1999 | Colella et al. |
| 6,009,333 A | 12/1999 | Chaco |
| 6,021,392 A | 2/2000 | Lester et al. |
| 6,024,699 A | 2/2000 | Surwit et al. |
| 6,032,155 A | 2/2000 | de la Huerga |
| 6,039,251 A | 3/2000 | Holowko et al. |
| 6,047,203 A | 4/2000 | Sackner et al. |
| 6,048,087 A | 4/2000 | Laurent et al. |
| 6,053,887 A | 4/2000 | Levitas et al. |
| 6,063,026 A | 5/2000 | Schauss et al. |
| 6,082,776 A | 7/2000 | Feinberg |
| 6,112,182 A | 8/2000 | Akers et al. |
| RE36,871 E | 9/2000 | Epstein et al. |
| 6,112,526 A | 9/2000 | Chase |
| 6,134,582 A | 10/2000 | Kennedy |
| 6,135,949 A | 10/2000 | Russo et al. |
| 6,202,923 B1 | 3/2001 | Boyer et al. |
| 6,228,057 B1 | 5/2001 | Vasko |
| 6,241,704 B1 | 6/2001 | Peterson et al. |
| 6,269,340 B1 | 7/2001 | Ford et al. |
| 6,282,441 B1 | 8/2001 | Raymond et al. |
| 6,290,681 B1 | 9/2001 | Brown |
| 6,292,698 B1 | 9/2001 | Duffin et al. |
| 6,302,844 B1 | 10/2001 | Walker et al. |
| 6,312,378 B1 | 11/2001 | Bardy |
| 6,314,556 B1 | 11/2001 | DeBusk et al. |
| 6,319,200 B1 | 11/2001 | Lai et al. |
| 6,322,502 B1 | 11/2001 | Schoenberg et al. |
| 6,338,007 B1 | 1/2002 | Broadfield et al. |
| 6,339,732 B1 | 1/2002 | Phoon et al. |
| 6,406,426 B1 | 6/2002 | Reuss et al. |
| 6,409,684 B1 | 6/2002 | Wilk |
| 6,421,650 B1 | 7/2002 | Goetz et al. |
| 6,493,747 B2 | 12/2002 | Simmon et al. |
| 6,519,569 B1 | 2/2003 | White et al. |
| 6,529,892 B1 | 3/2003 | Lambert |
| 6,540,672 B1 | 4/2003 | Simonsen et al. |
| 6,558,352 B1 | 5/2003 | Hogan |
| 6,581,606 B2 | 6/2003 | Kutzko et al. |
| 6,671,563 B1 * | 12/2003 | Engelson ............... G06Q 50/22 700/2 |
| 6,745,764 B2 | 6/2004 | Hickle |
| 6,757,898 B1 | 6/2004 | Ilsen et al. |
| 6,785,589 B2 | 8/2004 | Eggenberger et al. |
| 6,796,956 B2 | 9/2004 | Hartlaub et al. |
| 6,799,149 B2 | 9/2004 | Hartlaub |
| 6,847,861 B2 | 1/2005 | Lunak et al. |
| 6,856,247 B1 | 2/2005 | Wallace |
| 6,993,402 B2 | 1/2006 | Klass et al. |
| 7,034,691 B1 | 4/2006 | Rapaport et al. |
| 7,054,844 B2 | 5/2006 | Fletcher et al. |
| 7,096,072 B2 | 8/2006 | Engleson et al. |
| 7,215,991 B2 | 5/2007 | Besson et al. |
| 7,229,430 B2 | 6/2007 | Hickle et al. |
| 7,230,529 B2 | 6/2007 | Ketcherside, Jr. et al. |
| 7,256,708 B2 | 8/2007 | Rosenfeld et al. |
| 7,263,492 B1 | 8/2007 | Suresh et al. |
| 7,379,885 B1 | 5/2008 | Zakim |
| 7,384,420 B2 | 6/2008 | Dycus et al. |
| 7,398,183 B2 | 7/2008 | Holland et al. |
| 7,421,709 B2 | 9/2008 | Watson et al. |
| 7,433,853 B2 | 10/2008 | Brockway et al. |
| 7,471,994 B2 | 12/2008 | Ford et al. |
| 7,526,769 B2 | 4/2009 | Watts, Jr. et al. |
| 7,587,415 B2 | 9/2009 | Gaurav et al. |
| 7,612,679 B1 | 11/2009 | Fackler et al. |
| 7,693,697 B2 | 4/2010 | Westenskow et al. |
| 7,769,601 B1 | 8/2010 | Bleser et al. |
| 7,771,385 B2 | 8/2010 | Eggers et al. |
| 7,771,386 B2 | 8/2010 | Eggers et al. |
| 7,787,946 B2 | 8/2010 | Stahmann et al. |
| 7,796,045 B2 | 9/2010 | Spear et al. |
| 7,835,927 B2 | 11/2010 | Schlotterbeck et al. |
| 7,847,970 B1 | 12/2010 | McGrady |

(56) References Cited

U.S. PATENT DOCUMENTS

| | | |
|---|---|---|
| 7,860,583 B2 | 12/2010 | Condurso et al. |
| 7,962,544 B2 | 6/2011 | Torok et al. |
| 7,970,550 B2 | 6/2011 | Arakelyan et al. |
| 7,983,995 B2 | 7/2011 | Murphy et al. |
| 8,005,688 B2 | 8/2011 | Coffman et al. |
| 8,024,200 B2 | 9/2011 | Jennings et al. |
| 8,160,895 B2 | 4/2012 | Schmitt et al. |
| 8,197,437 B2 | 6/2012 | Kalafut et al. |
| 8,284,059 B2 | 10/2012 | Ross |
| 8,291,337 B2 | 10/2012 | Gannin et al. |
| 8,340,792 B2 | 12/2012 | Condurso et al. |
| 8,689,008 B2 | 4/2014 | Rangadass et al. |
| 2001/0037083 A1 | 11/2001 | Hartlaub et al. |
| 2001/0044731 A1 | 11/2001 | Coffman et al. |
| 2002/0010679 A1 | 1/2002 | Felsher |
| 2002/0016568 A1 | 2/2002 | Lebel et al. |
| 2002/0016923 A1 | 2/2002 | Knaus et al. |
| 2002/0022973 A1 | 2/2002 | Sun et al. |
| 2002/0026223 A1 | 2/2002 | Riff et al. |
| 2002/0033548 A1 | 3/2002 | Brodkin et al. |
| 2002/0035484 A1 | 3/2002 | McCormick |
| 2002/0038392 A1 | 3/2002 | De La Huerga |
| 2002/0042636 A1 | 4/2002 | Koshiol et al. |
| 2002/0046346 A1 | 4/2002 | Evans |
| 2002/0077849 A1 | 6/2002 | Baruch et al. |
| 2002/0087114 A1 | 7/2002 | Hartlaub |
| 2002/0116509 A1 | 8/2002 | DeLaHuerga |
| 2002/0120350 A1 | 8/2002 | Klass et al. |
| 2002/0169636 A1 | 11/2002 | Eggers et al. |
| 2002/0198624 A1 | 12/2002 | Greenwald et al. |
| 2003/0009244 A1 | 1/2003 | Engleson et al. |
| 2003/0036683 A1 | 2/2003 | Kehr et al. |
| 2003/0045858 A1 | 3/2003 | Struys et al. |
| 2003/0051737 A1 | 3/2003 | Hickle et al. |
| 2003/0063524 A1 | 4/2003 | Niemiec et al. |
| 2003/0069481 A1 | 4/2003 | Hervy et al. |
| 2003/0105389 A1 | 6/2003 | Noonan et al. |
| 2003/0105555 A1 | 6/2003 | Lunak et al. |
| 2003/0106553 A1 | 6/2003 | Vanderveen |
| 2003/0114836 A1 | 6/2003 | Estes et al. |
| 2003/0121517 A1 | 7/2003 | McFarland |
| 2003/0129578 A1 | 7/2003 | Mault |
| 2003/0135087 A1 | 7/2003 | Hickle et al. |
| 2003/0135388 A1 | 7/2003 | Martucci et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0149599 A1 | 8/2003 | Goodall et al. |
| 2003/0156143 A1 | 8/2003 | Westenskow et al. |
| 2003/0158746 A1 | 8/2003 | Forrester |
| 2003/0163223 A1 | 8/2003 | Blomquist |
| 2003/0205897 A1 | 11/2003 | Kaufman |
| 2003/0236683 A1 | 12/2003 | Henderson et al. |
| 2004/0068229 A1 | 4/2004 | Jansen et al. |
| 2004/0073329 A1 | 4/2004 | Engleson et al. |
| 2004/0107118 A1 | 6/2004 | Harnsberger et al. |
| 2004/0122702 A1 | 6/2004 | Sabot et al. |
| 2004/0122705 A1 | 6/2004 | Sabot et al. |
| 2004/0122719 A1 | 6/2004 | Sabot et al. |
| 2004/0122790 A1 | 6/2004 | Walker et al. |
| 2004/0128162 A1 | 7/2004 | Schlotterbeck et al. |
| 2004/0152622 A1 | 8/2004 | Keith et al. |
| 2004/0167465 A1 | 8/2004 | Mihai et al. |
| 2004/0167804 A1 | 8/2004 | Simpson et al. |
| 2004/0172283 A1 | 9/2004 | Vanderveen et al. |
| 2004/0172300 A1 | 9/2004 | Mihai et al. |
| 2004/0172302 A1 | 9/2004 | Martucci et al. |
| 2004/0176297 A1 | 9/2004 | Cheung et al. |
| 2004/0188998 A1 | 9/2004 | Henthorn |
| 2004/0193325 A1 | 9/2004 | Bonderud et al. |
| 2004/0193446 A1 | 9/2004 | Mayer et al. |
| 2004/0260478 A1 | 12/2004 | Schwamm |
| 2005/0010166 A1 | 1/2005 | Hickle |
| 2005/0020996 A1 | 1/2005 | Hartlaub et al. |
| 2005/0021297 A1 | 1/2005 | Hartlaub |
| 2005/0033606 A1 | 2/2005 | Miller |
| 2005/0049179 A1 | 3/2005 | Davidson et al. |
| 2005/0055242 A1 | 3/2005 | Bello et al. |
| 2005/0088296 A1 | 4/2005 | Lee |
| 2005/0096941 A1 | 5/2005 | Tong |
| 2005/0097566 A1 | 5/2005 | Watts et al. |
| 2005/0107914 A1 | 5/2005 | Engleson et al. |
| 2005/0108057 A1 | 5/2005 | Cohen et al. |
| 2005/0113945 A1 | 5/2005 | Engleson et al. |
| 2005/0119788 A1 | 6/2005 | Engleson et al. |
| 2005/0144043 A1 | 6/2005 | Holland et al. |
| 2005/0145010 A1 | 7/2005 | Vanderveen et al. |
| 2005/0148890 A1 | 7/2005 | Hastings |
| 2005/0171815 A1 | 8/2005 | Vanderveen |
| 2005/0224083 A1 | 10/2005 | Crass et al. |
| 2005/0278194 A1 | 12/2005 | Holland et al. |
| 2006/0026205 A1 | 2/2006 | Butterfield |
| 2006/0047538 A1 | 3/2006 | Condurso et al. |
| 2006/0053036 A1 | 3/2006 | Coffman et al. |
| 2006/0101072 A1 | 5/2006 | Busche et al. |
| 2006/0122481 A1 | 6/2006 | Sievenpiper et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0217628 A1 | 9/2006 | Huiku |
| 2006/0218015 A1 | 9/2006 | Walker et al. |
| 2006/0229551 A1 | 10/2006 | Martinez et al. |
| 2006/0249423 A1 | 11/2006 | Reijonen |
| 2006/0271401 A1 | 11/2006 | Lassetter et al. |
| 2006/0287890 A1 | 12/2006 | Stead et al. |
| 2007/0015972 A1 | 1/2007 | Wang et al. |
| 2007/0043767 A1 | 2/2007 | Osborne et al. |
| 2007/0061266 A1 | 3/2007 | Moore et al. |
| 2007/0061393 A1 | 3/2007 | Moore |
| 2007/0083389 A1 | 4/2007 | Dyer et al. |
| 2007/0106457 A1 | 5/2007 | Rosenberg |
| 2007/0106753 A1 | 5/2007 | Moore |
| 2007/0106754 A1 | 5/2007 | Moore |
| 2007/0129647 A1 | 6/2007 | Lynn |
| 2007/0156860 A1 | 7/2007 | Nedelcu et al. |
| 2007/0168301 A1 | 7/2007 | Eisner et al. |
| 2007/0185615 A1 | 8/2007 | Bossi et al. |
| 2007/0208454 A1 | 9/2007 | Forrester et al. |
| 2007/0210157 A1 | 9/2007 | Miller |
| 2007/0286466 A1 | 12/2007 | Heffernan et al. |
| 2007/0293843 A1 | 12/2007 | Ireland et al. |
| 2008/0015549 A1 | 1/2008 | Maughan |
| 2008/0025230 A1 | 1/2008 | Patel et al. |
| 2008/0034323 A1 | 2/2008 | Blomquist |
| 2008/0040151 A1 | 2/2008 | Moore |
| 2008/0046292 A1 | 2/2008 | Myers et al. |
| 2008/0141272 A1 | 6/2008 | Borgendale et al. |
| 2008/0162254 A1 | 7/2008 | Herger et al. |
| 2008/0164998 A1 | 7/2008 | Scherpbier et al. |
| 2008/0169045 A1 | 7/2008 | Tribble et al. |
| 2008/0195246 A1 | 8/2008 | Tribble et al. |
| 2008/0272138 A1 | 11/2008 | Ross et al. |
| 2008/0317672 A1 | 12/2008 | Viertio-Oja |
| 2009/0012812 A1 | 1/2009 | Rausch et al. |
| 2009/0012813 A1 | 1/2009 | Berzansky et al. |
| 2009/0054754 A1 | 2/2009 | McMahon et al. |
| 2009/0099867 A1 | 4/2009 | Newman |
| 2009/0112333 A1 | 4/2009 | Sahai |
| 2009/0150484 A1 | 6/2009 | Roberts |
| 2009/0210252 A1 | 8/2009 | Silver |
| 2009/0240651 A1 | 9/2009 | Fletcher et al. |
| 2009/0306585 A1 | 12/2009 | Pang et al. |
| 2009/0306944 A1 | 12/2009 | Willmann et al. |
| 2009/0319623 A1 | 12/2009 | Srinivasan et al. |
| 2010/0037067 A1 | 2/2010 | Rangadass et al. |
| 2010/0094653 A1 | 4/2010 | Tribble et al. |
| 2010/0121654 A1 | 5/2010 | Portnoy et al. |
| 2010/0161113 A1 | 6/2010 | Tribble et al. |
| 2010/0169120 A1 | 7/2010 | Herbst et al. |
| 2010/0169771 A1 | 7/2010 | Pelegrin et al. |
| 2010/0174552 A1 | 7/2010 | Hawkes et al. |
| 2010/0174553 A1 | 7/2010 | Kaufman et al. |
| 2010/0179825 A1 | 7/2010 | Hanov et al. |
| 2010/0241453 A1 | 9/2010 | Malec |

(56) References Cited

U.S. PATENT DOCUMENTS

| | | |
|---|---|---|
| 2010/0241456 A1 | 9/2010 | Miller et al. |
| 2010/0271218 A1 | 10/2010 | Hoag et al. |
| 2010/0280840 A1 | 11/2010 | Fukushi et al. |
| 2010/0323397 A1 | 12/2010 | Reavy et al. |
| 2011/0015941 A1 | 1/2011 | Backhaus |
| 2011/0046975 A1 | 2/2011 | Hoffman |
| 2011/0060758 A1 | 3/2011 | Schlotterbeck et al. |
| 2011/0119612 A1 | 5/2011 | Gannon et al. |
| 2011/0179405 A1 | 7/2011 | Dicks et al. |
| 2011/0202495 A1 | 8/2011 | Gawlick |
| 2011/0282691 A1 | 11/2011 | Coffman et al. |
| 2011/0288882 A1 | 11/2011 | Halow |
| 2011/0313787 A1 | 12/2011 | Rangadass et al. |
| 2012/0011253 A1 | 1/2012 | Friedman et al. |
| 2012/0016215 A1 | 1/2012 | Condurso et al. |
| 2012/0041775 A1 | 2/2012 | Cosentino et al. |
| 2012/0053533 A1 | 3/2012 | Butterfield et al. |
| 2012/0075061 A1 | 3/2012 | Barnes |
| 2012/0136673 A1 | 5/2012 | Presley et al. |
| 2012/0173264 A1 | 7/2012 | Brush et al. |
| 2012/0179006 A1 | 7/2012 | Jansen et al. |
| 2012/0182939 A1 | 7/2012 | Rajan et al. |
| 2012/0185267 A1 | 7/2012 | Kamen et al. |
| 2012/0191052 A1 | 7/2012 | Rao |
| 2012/0239824 A1 | 9/2012 | Nguyen et al. |
| 2012/0241043 A1 | 9/2012 | Perazzo et al. |
| 2012/0247480 A1 | 10/2012 | Varga |
| 2012/0253835 A1 | 10/2012 | Tracy et al. |
| 2012/0265549 A1 | 10/2012 | Virolainen |
| 2013/0018356 A1 | 1/2013 | Prince et al. |
| 2013/0085771 A1 | 4/2013 | Ghanbari et al. |
| 2013/0096444 A1 | 4/2013 | Condurso et al. |
| 2013/0197927 A1 | 8/2013 | Vanderveen et al. |
| 2013/0197928 A1 | 8/2013 | Vanderveen et al. |
| 2013/0197929 A1 | 8/2013 | Vanderveen et al. |
| 2013/0197930 A1 | 8/2013 | Garibaldi et al. |
| 2013/0197931 A1 | 8/2013 | Gupta et al. |
| 2013/0204433 A1 | 8/2013 | Gupta et al. |
| 2013/0204637 A1 | 8/2013 | Vanderveen et al. |
| 2013/0262138 A1 | 10/2013 | Jaskela et al. |
| 2014/0028464 A1 | 1/2014 | Garibaldi |
| 2014/0031976 A1 | 1/2014 | Reinhardt et al. |
| 2014/0100868 A1 | 4/2014 | Condurso et al. |
| 2014/0278466 A1 | 9/2014 | Simmons et al. |
| 2014/0297313 A1 | 10/2014 | Condurso et al. |
| 2014/0350950 A1 | 11/2014 | Jaskela et al. |
| 2015/0250948 A1 | 9/2015 | Gupta et al. |
| 2016/0000997 A1 | 1/2016 | Batch et al. |

FOREIGN PATENT DOCUMENTS

| | | | |
|---|---|---|---|
| CN | 1421810 A | | 6/2003 |
| CN | 1759398 A | | 4/2006 |
| CN | 1803103 A | | 7/2006 |
| CN | 101116077 A | | 1/2008 |
| CN | 101146055 A | | 3/2008 |
| CN | 201110955 Y | | 9/2008 |
| CN | 101331491 A | | 12/2008 |
| CN | 101689320 A | | 3/2010 |
| CN | 101890193 A | | 11/2010 |
| CN | 102068725 A | | 5/2011 |
| CN | 102508877 A | | 6/2012 |
| CN | 102521394 A | | 6/2012 |
| CN | 102688532 A | | 9/2012 |
| CN | 102799783 A | | 11/2012 |
| DE | 4023785 A1 | | 1/1992 |
| EP | 0192786 A2 | | 9/1986 |
| EP | 0384155 A2 | | 8/1990 |
| EP | 0595474 A2 | | 5/1994 |
| EP | 0649316 A1 | | 4/1995 |
| EP | 0652528 A2 | | 5/1995 |
| EP | 0784283 A1 | | 7/1997 |
| EP | 0921488 A1 | | 6/1999 |
| EP | 1003121 A2 | | 5/2000 |
| EP | 1018347 A2 | | 7/2000 |
| EP | 1237113 A2 | | 9/2002 |
| GB | 2 141 006 A | | 12/1984 |
| JP | 62114562 | | 5/1987 |
| JP | 11505352 | | 5/1999 |
| JP | 2002520718 A | | 7/2002 |
| JP | 2003085283 A | | 3/2003 |
| JP | 2004287616 A | | 10/2004 |
| JP | 2005165442 A | | 6/2005 |
| JP | 2005296428 A | | 10/2005 |
| JP | 2006155070 A | | 6/2006 |
| JP | 2006521183 A | | 9/2006 |
| JP | 2008508616 A | | 3/2008 |
| JP | 2008516303 A | | 5/2008 |
| JP | 2011501311 A | | 1/2011 |
| JP | 2012200430 A | | 10/2012 |
| JP | 5168708 B2 | | 3/2013 |
| KR | 1020070045611 | | 5/2007 |
| KR | 1020080013129 A | | 2/2008 |
| KR | 100847397 B1 | | 7/2008 |
| KR | 1020100125972 A | | 12/2010 |
| KR | 1020110070824 A | | 6/2011 |
| KR | 1020120076615 A | | 7/2012 |
| KR | 1020120076635 A | | 7/2012 |
| NZ | 522631 A | | 7/2004 |
| WO | WO-1993022735 A1 | | 11/1993 |
| WO | WO-1994005344 A1 | | 3/1994 |
| WO | WO-2000003344 | | 3/1994 |
| WO | WO-1994008647 A1 | | 4/1994 |
| WO | WO-1994013250 A1 | | 6/1994 |
| WO | WO-1995023378 A2 | | 8/1995 |
| WO | WO-199620745 A1 | | 7/1996 |
| WO | WO-1996020745 A1 | | 7/1996 |
| WO | WO-199625214 A1 | | 8/1996 |
| WO | WO-1996025214 A1 | | 8/1996 |
| WO | WO-1996036923 A1 | | 11/1996 |
| WO | WO-1997004712 A1 | | 2/1997 |
| WO | WO-1998013783 A1 | | 4/1998 |
| WO | WO-1998028676 A2 | | 7/1998 |
| WO | WO-1999009505 A1 | | 2/1999 |
| WO | WO-1999010829 A1 | | 3/1999 |
| WO | WO-1999010830 A1 | | 3/1999 |
| WO | WO-1999035588 A1 | | 7/1999 |
| WO | WO-1999044167 A1 | | 9/1999 |
| WO | WO-1999045490 A2 | | 9/1999 |
| WO | WO-1999046718 A1 | | 9/1999 |
| WO | WO-1999067732 A1 | | 12/1999 |
| WO | WO-2000004521 A1 | | 1/2000 |
| WO | WO-2000018449 A2 | | 4/2000 |
| WO | WO-2000032088 A1 | | 6/2000 |
| WO | WO-2000032098 A1 | | 6/2000 |
| WO | WO-2001086506 A1 | | 11/2001 |
| WO | WO-2001088828 A2 | | 11/2001 |
| WO | WO-2002036044 A2 | | 5/2002 |
| WO | WO-2002069099 | | 9/2002 |
| WO | WO-2003038566 A2 | | 5/2003 |
| WO | WO-2003053503 A1 | | 7/2003 |
| WO | WO-2003092769 | | 11/2003 |
| WO | WO-2003094091 A1 | | 11/2003 |
| WO | WO-2004060443 A2 | | 7/2004 |
| WO | WO-2004061745 A2 | | 7/2004 |
| WO | WO-2010124016 A1 | | 10/2010 |
| WO | WO-2010124328 A1 | | 11/2010 |
| WO | WO-2012095829 A2 | | 7/2012 |
| WO | WO-2014159280 A1 | | 10/2014 |

OTHER PUBLICATIONS

Chinese Office Action for Application No. 201480015025.7, dated Jun. 24, 2019, 25 pages.
Chinese Office Action for Application No. 201480015036.5, dated Jun. 24, 2019, 20 pages.
European Summons to attend oral proceedings pursuant to Rule 115(1) EPC for Application No. 14772937.0, dated Jul. 17, 2019, 12 pages.
Canadian Office Action for Application No. 2828898, dated Dec. 7, 2018, 5 pages.
Australian Office Action for Application No. 2014241019, dated Aug. 12, 2019, 4 pages.

(56) References Cited

OTHER PUBLICATIONS

Australian Office Action for Application No. 2014241022, dated Jun. 25, 2019, 3 pages.
Australian Office Action for Application No. 2018232958, dated Aug. 7, 2019, 3 pages.
Chinese Office Action for Application No. 201480015093.3, dated Apr. 25, 2019, 18 pages.
Chinese Office Action for Application No. 201480041985.0, dated Apr. 3, 2019, 12 pages.
Japanese Office Action for Application No. 2016-501081, dated May 7, 2019, 4 pages.
"General-Purpose Infusion Pumps," Evaluation—Health Devices, Oct. 2002, pp. 353-387, vol. 31 (10), ECRI Institute.
"Infusion Pump Technology," Health Devices, Apr.-May 1998, pp. 150-170, vol. 27(4-5), ECRI Institute.
"Infusion Pumps, General Purpose," Healthcare Product Comparison System, 2007, pp. 1-54, ECRI Institute.
"Infusion Pumps, Large-Volume," Healthcare Product Comparison System, 2010, pp. 1-51, ECRI Institute.
"Smart Infusion Pumps Join CPOE and Bar Coding as Important Ways to Prevent Medication Errors," ISMP—Medication Safety Alert, Feb. 7, 2002, 2 pgs., Institute for Safe Medication Practices.
Anonymous, Guardrails® Safety Software—Medley TM Medication Safety System, Alaris Medical Systems XP-00234431; 2002 Alaris Medical Systems Inc. Nov. 2002, SSM @2159C.
Baldauf-Sobez et al., "How Siemens' Computerized Physician Order Entry Helps Prevent the Human Errors," electromedica, vol. 71, No. 1, 2003, pp. 2-10.
Eskew, James et al., Using Innovative Technologies to Set New Safety Standards for the Infusion of Intravenous Medications, Hospital Pharmacy, vol. 37, No. 11, pp. 1179-1189, 2002, Facts and Comparisons.
Kohn, et al., "To Err is Human—Building a Safer Health System," National Academy Press, 2002, pp. i-287, National Academy of Sciences.
Lesar, "Recommendations for Reducing Medication Errors," Medscape Pharamcists, posted Jul. 24, 2000, 10 pgs, vol. 1(2), Medscape Pharamcists, <http://www.medscape.com>.
Meier, "Hospital Products Get Seal of Approval at a Price," The New York Times, Apr. 23, 2002, 5 pgs.
Queensland Health. Use of returned or unused dispensed medicines, Jan. 5, 2005, Queensland Government. pp. 1-2.
Shabot et al., "Wireless clinical alerts for critical medication, laboratory and physiologic data," System Sciences 2000. Proceedings of the 33rd Annual Conference on Jan. 4-7, 2000, Piscataway, NJ, IEEE, Jan. 4, 2000.
Williams, et al., "Reducing the Risk of User Error with Infusion Pumps," Professional Nurse—Safe Practice—Infusion Devices, Mar. 2000, pp. 382-384, vol. 15(6).
Yokoi, "Prevention of Errors in Injection/Drip Infusion—No excuse for ignorance!—Essential Points of Accident Prevention, IV Infusion Pump, Syringe-pump Accident Prevention," JIN Special, Igaku Shoin K.K., Dec. 1, 2001, pp. 109-120, No. 70.
Calabrese, et al., "Medication administration errors in adult patients in the ICU," Intensive Care Med, 2001, pp. 1592-1598, vol. 27, Springer-Verlag.
Chinese Office Action for Application No. 2012800136388, dated Jul. 18, 2016, 2 pages excluding machine translation.
Extended European Search Report for Application No. 14779655.1, dated Jul. 14, 2016, 8 pages.
Extended European Search Report for Application No. 14780320.9, dated Jul. 1, 2016, 7 pages.
Extended European Search Report for Application No. 14775918.7, dated Sep. 13, 2016, 10 pages.
Evans, R. S. et al., "Enhanced notification of infusion pump programming errors", Studies in health technology and informatics, Jan. 1, 2010, pp. 734-738, XP055305644, Netherlands DOI: 10.3233/978-1-60750-588-4-734 Retrieved from the Internet: URL:http://booksonline.iospress.nl/Extern/EnterMedLine.aspx?ISSN=0926-9630&Volume=160&SPage=734 [retrieved on Sep. 26, 2016].
Extended European Search Report and Written Opinion for Application No. 14772937.0, dated Oct. 10, 2016, 9 pages.
Extended European Search Report and Written Opinion for Application No. 14779139.6, dated Nov. 7, 2016, 7 pages.
Extended European Search Report for Application No. 14801713.0, dated Jan. 16, 2017, 8 pages.
Canadian Office Action for Application No. 2512991, dated Mar. 2, 2017, 4 pages.
Extended European Search Report for Application No. 14801726.2, dated Jan. 5, 2017, 8 pages.
Chinese Office Action for Application No. 201480015147.6, dated Mar. 10, 2017, 10 pages excluding translation.
Canadian Office Action for Application No. 2551903, dated Mar. 28, 2017, 7 pages.
European Office Action for Application No. 12756903.6, dated Apr. 19, 2017, 5 pages.
Office Action for United Arab Emirates Application No. UAE/P/0962/2013, dated Apr. 17, 2017, 18 pages.
Canadian Office Action for Application No. 2512991, dated Jan. 10, 2018, 4 pages.
Canadian Office Action for Application No. 2828898, dated Jan. 11, 2018, 8 pages.
Chinese Office Action for Application No. 201480015025.7, dated Jan. 23, 2018, 11 pages excluding English summary.
Chinese Office Action for Application No. 201480015036.5, dated Jan. 23, 2018, 13 pages excluding English translation.
Japanese Office Action in Application No. 2016-501081, dated Feb. 9, 2018, 4 pages.
Memo concerning Mexican Office Action for Application No. MX/a/2015/015959, memo dated Mar. 2, 2018, 1 page.
Written Opinion for Application No. PCT/US2006/004864, dated Jun. 22, 2006, 5 pages.
New Zealand Examination Report for Application No. 560278, dated Jun. 23, 2009, 1 page.
Canadian Office Action for Application No. 2596881, dated Dec. 20, 2012, 1 page.
Australian Office Action for Application No. 2006213718, dated Sep. 19, 2011, 3 pages.
Australian Office Action for Application No. 2006213718, dated Jul. 8, 2010, 4 pages.
European Office Action for Application No. 06720651.6, dated May 5, 2008, 3 pages.
Chinese Office Action for Application No. 201480015093.3, dated Jul. 16, 2018, 16 pages.
Canadian Office Action for Application No. 2551903, dated Mar. 5, 2018, 8 pages.
Chinese Office Action for Application No. 201480015025.7, dated Oct. 9, 2018, 27 pages.
Chinese Office Action for Application No. 201480015036.5, dated Sep. 29, 2018, 20 pages.
Chinese Office Action for Application No. 201480015147.6, dated May 3, 2018, 6 pages.
Chinese Office Action for Application No. 201480041362.3, dated Oct. 18, 2018, 13 pages.
European Office Action for Application No. 14772937.0, dated Apr. 19, 2018, 9 pages.
European Office Action for Application No. 14779655.1, dated Mar. 8, 2018, 7 pages.
Japanese Office Action for Application No. 2016-501081, dated Nov. 2, 2018, 6 pages.
Australian Office Action for Application No. 2014241022, dated Feb. 7, 2019, 4 pages.
Australian Office Action for Application No. 2014241019, dated Feb. 6, 2019, 3 pages.
India Office Action for Application No. 7050/CHENP/2013, dated Sep. 18, 2019, 7 pages.
Australian Office Action for Application No. 2014241022, dated Sep. 30, 2019, 4 pages.
Chinese Office Action for Application No. 201480015036.5, dated Nov. 5, 2019, 12 pages.
Chinese Office Action for Application No. 201480041985.0, dated Sep. 23, 2019, 24 pages.

(56) References Cited

OTHER PUBLICATIONS

European Communication for Application No. 14779655.1, dated Oct. 2, 2019, 12 pages.
Japanese Office Action for Application No. 2016501081, dated Nov. 12, 2019, 6 pages.
U.S. Appl. No. 90/009,912, filed Aug. 12, 2013, Schlotterbeck et al.
U.S. Appl. No. 90/011,697, filed Aug. 12, 2013, Schlotterbeck et al.
Australian Office Action for Application No. 2014241019, dated Dec. 5, 2019, 5 pages.
Australian Office Action for Application No. 2014268828, dated Nov. 25, 2019, 3 pages.
Canadian Office Action for Application No. 2828898, dated Dec. 3, 2019, 6 pages.
Canadian Office Action for Application No. 2901024, dated Jan. 27, 2020, 5 pages.
Chinese Office Action for Application No. 201480015025.7, dated Nov. 12, 2019, 20 pages.
Chinese Office Action for Application No. 201480015093.3, dated Dec. 4, 2019, 17 pages.
European Office Action for Application No. 14801713.0, dated Dec. 11, 2019, 6 pages.
United Arab Emirates Office Action from KIPO for Application No. UAE/P/1554/2015, dated Nov. 21, 2019, 11 pages.
Canada Office Action for Application No. 2900564, dated Jan. 28, 2020, 4 pages.
Brazil Office Action for Application No. BR112015029135-0, dated Feb. 12, 2020, 5 pages.
Brazil Office Action for Application No. BR112015019758-2, dated Feb. 20, 2020, 5 pages.

\* cited by examiner

MANAGEMENT OF PENDING MEDICATION ORDERS

CROSS REFERENCE TO RELATED APPLICATIONS

This application is a continuation of U.S. patent application Ser. No. 14/848,063, entitled "MANAGEMENT OF PENDING MEDICATION ORDERS", filed Sep. 8, 2015, which is a continuation of U.S. patent application Ser. No. 11/326,145, entitled "MANAGEMENT OF PENDING MEDICATION ORDERS," filed Dec. 30, 2005, which claims the benefit of U.S. Provisional Patent Application No. 60/652,382, entitled "MANAGEMENT OF PENDING MEDICATION ORDERS," filed on Feb. 11, 2005, the disclosures of all of which are incorporated herein by reference in their entirety.

BACKGROUND

The present invention relates generally to medication management systems and methods, and more particularly, to managing pending medication orders and controlled medications.

Physicians and other medication personnel apply intravenous ("IV") infusion therapy to treat various medication complications in patients. IV infusion therapy typically involves infusing medication fluids, such as drugs or nutrients, from a fluid supply, such as a bag, bottle or other container, through the tube of a fluid administration set to a cannula inserted into a patient's blood vessel. Other medications may be ordered by a physician for a patient, such as pills or liquids, to be taken orally by the patient. In some cases, a physician may order multiple medications for a single patient, and these are to be administered at particular times of a day or over a number of days resulting in a list of "pending medication orders" for the patient. In some cases, the administration of multiple medications must occur sequentially and in other cases, there is an overlap of the administration of medications. In yet other cases, the administration of certain medications must occur at a certain time before or after the administration of another medication or medications.

In a typical facility, a physician enters an order for medication for a particular patient. This order may be handled either as a simple prescription slip, or it may be entered into an automated system, such as a physician order entry ("POE") system. The prescription slip or the electronic prescription from the POE system is routed to the pharmacy, where the order is checked, then filled. For medication that is to be delivered by IV, the prescribed medication is prepared by a pharmacist and added to a bag, bottle, or other medication container (such as a syringe) at a pharmacy. A pharmacist also typically identifies the prepared order, identifying the contents of the container and the patient for whom the container is intended with a written paper label that is attached to the container and in some cases by other means, such as including a bar code or magnetic device, or by use of a radio frequency ("RF") signal interactive device such as an RFID tag, as examples. The prepared medication is then delivered to a nurse's station for subsequent administration to the patient.

For safety reasons and in order to achieve optimal results, the medical fluid is often administered in accurate amounts as prescribed by the doctor and in a controlled fashion by using an IV infusion pump. Infusion pumps operate by displacing the fluid located in a fluid administration set to force fluid from the fluid supply through the tube and into the patient. The infusion pump is programmed by an operator such as a nurse or other medical personnel or clinician, with operating parameters to achieve the administration of the drug as prescribed by the physician. Such operating, or pumping, parameters are drug and patient specific. That is, the pumping parameters are selected based on the particular drug prescribed and the specific patient for whom they are intended. It is the nurse's responsibility to match the prescribed drug with the correct patient and with the properly programmed pump at the correct time for administration of the medication.

Hospitals and other institutions continually strive to provide quality patient care. Medication errors, such as when a patient receives the wrong drug or receives the correct drug at the wrong time or in the wrong dosage, are significant problems for all health care facilities. In the administration of medication, focus is typically directed to the following five "rights" or factors: the right patient, the right drug, the right route, the right amount, and the right time. The nurse aims to ensure that these "rights" are accomplished. Systems and methods seeking to reduce medication errors should also take these five "rights" into consideration.

In some cases, a single patient may be prescribed multiple simultaneous infusions for different medications, sometimes four or more, which requires multiple infusion pumps that may all be programmed differently. Prior attempts have been made to assure that the right medication is administered to the right patient through the right pump. In one example, a bar code label identifying the medication and patient is applied to the bag at the pharmacy. After an operator such as a nurse manually programs the pump, a bar code scanner connected to the pump is used to read the bar code label on the bag to verify that it identifies the same medication as that programmed into the pump. In another example, U.S. Pat. No. 5,078,683 to Sancoff et al. discloses a bar code label applied to the bag that is read with a bar code scanner to automatically program the pump, thus avoiding manual programming entirely. This feature of automatic programming or automatically populating the fields of the pumping parameters of the infusion pump can provide a significant benefit to busy clinicians, and can increase the accuracy of pump programming.

Advanced infusion pumps have revolutionized the way intravenous IV medications are delivered by providing dose limit protection, ensuring "right" dose. Still missing from these pumps in a non-networked environment is the ability to automatically select the "right" medication from the pump's drug library, ensure that the drug that is being administered is for the patient that is currently connected to the pump, and that the caregiver administering the drug is authorized to do so.

In the environment of intensive care units, cardiac care units, operating rooms, or trauma centers, it is often necessary to infuse into the patient multiple medications simultaneously. In addition, some of the medications used in these environments are not directly compatible with each other and therefore need to be infused into the patient at different points of the body. Recently, infusion pumps capable of infusing several medications at different rates into a patient have been developed. While some types of these pumps are designed to deliver the medications through a common cannula, others are designed with multiple pumps, or channels, that pump fluid into a patient through a plurality of infusion lines. On such pump is the Medley medication safety system from ALARIS Products of Cardinal Health, San Diego, Calif., U.S.A., that provides this level of protection in a networked environment and a non-networked environment.

As the name implies, multi-channel infusion pumps have more than one pumping channel, and a separate infusion line or administration set is installed into each channel. This arrangement allows each pump to be programmed to deliver the particular medication that flows through the infusion line or set installed in the channel such that each line may deliver mediation at different rates or in different volumes. One problem that exists when infusing a patient with multiple infusion medications being delivered through different infusion lines is that it is necessary to ensure that each channel of the infusion pump is properly programmed to deliver each medication. A distinct advantage exists in using a single controller to program multiple infusion pumps, or channels, to deliver various medications to the patient. The interface is the same for all channels and the controller is in the same location for all channels. Where four or more channels are present and all must be operated simultaneously, a substantial amount of programming can be involved. A need exists for making such programming an easier task yet preserving safety in medication delivery.

Medication errors, that is, errors that occur in the ordering, dispensing, and administration of medications, regardless of whether those errors caused injury or not, are a significant consideration in the delivery of healthcare in the institutional setting. Additionally, adverse drug events ("ADE"), which are a subset of medication errors, defined as injuries involving a drug that require medical intervention, and representing some of the most serious medication errors, are responsible for a number of patient injuries and death. Healthcare facilities continually search for ways to reduce the occurrence of medication errors. Various systems and methods are being developed at present to reduce the frequency of occurrence and severity of preventable adverse drug events ("PADE") and other medication errors.

Most hospitals today have a pharmacy equipped with a computerized system for entering, preparing, and tracking prescriptions, managing drug inventory, checking for drug incompatibilities, and printing prescription orders and labels. Various solutions for increasing medication delivery safety have been proposed, such as systems that use bar codes to identify patients and medications, or systems allowing the beside entry of patient data. While these systems have advanced the art significantly, even more comprehensive systems could prove to be of greater value.

Typically, medications are delivered to a nurse station in a drug cart or other carrier that allows a certain degree of security to prevent theft or other loss of medications. In one example, the drug cart or carrier is divided into a series of drawers or containers, each container holding the prescribed medication for a single patient. To access the medication, the nurse must enter the appropriate identification to unlock a drawer, door, or container. In other situations, inventories of commonly-used drugs may be placed in a secure cabinet located in an area at or close by a nurse station. This inventory may contain not only topical medications but oral, IM-, and IV-delivered medications as well. Nurse identification and a medication order number are typically required to gain access to the cabinet. The nurse station receives a listing of drugs to be delivered to patients at intervals throughout the day. A nurse or other clinician reads the list of medications to be delivered, and gathers those medications from the inventory at the nurse station. Once all of the medications have been gathered for the patients in the unit for which the nurse station is responsible, one or more nurses then take the medications to the individual patients and administer the dosages.

Such a system though may not be capable of thoroughly verifying that the appropriate regimen is being delivered to a patient in the case where IV drugs are being delivered. For example, a nurse may carry an IV bag to a particular patient area, hang the bag, program an infusion pump with appropriate treatment parameters, and begin infusion of the medication. The applicable hospital control system, such as the pharmacy information system, may not know that the patient has received the medication, and if the information is lost somewhere, the possibility exists of medicating the patient twice. Thus, there may be a break in the link of verification that the medication is being properly delivered to the patient if an event occurs resulting in a deviation from the desired treatment parameters.

Moreover, even where the right medication arrives at the right patient for administration, incorrect administration of the medication may occur where the medication is to be administered using an automated or semi-automated administration device, such as an infusion pump, if the automated device is programmed with incorrect medication administration parameters. For example, even where the medication order includes the correct infusion parameters, those parameters may be incorrectly entered into an infusion pump, causing the infusion pump to administer the medication in a manner that may not result in the prescribed treatment. The nurse may also start an infusion at the wrong time or forget to administer an infusion, resulting in incorrect treatment that may interfere with other scheduled medications prescribed by the physician.

One attempt at providing a system with built-in safeguards to prevent the incorrect entry of treatment parameters utilizes a customizable drug library which is capable of monitoring the parameter entry process and interacting with the clinician should an incorrect entry or an out-of-range entry be attempted. In such a case, an alert is communicated to the clinician that the parameter entered is either incorrect or out of an appropriate range for that medication as established by the institution where care is being provided. Such a system contributes to a large increase in patient safety. However, further increases in safety and data communication and availability are desired so that busy clinicians have needed data readily at hand.

Hence, those skilled in the art have recognized that a need exists to more accurately ensure that correct medications are provided to a patient. A further need exists to more accurately ensure that correct infusions are provided to a patient at the correct pumping parameters. Further, those skilled in the art have recognized a need for providing more patient medication data to clinicians at the point of care of the patient. A still further need has been recognized for providing data concerning the administration of a medication. The present invention fulfills these needs and others.

SUMMARY OF THE INVENTION

Briefly and in general terms, the present invention is directed to displaying pending medication orders for a patient at a controller of an infusion pump once a patient has been identified by that controller. In another aspect, the invention is directed to presenting pending medication orders for a patient at an infusion controller at the point of care of the patient, and in another detailed aspect, the invention is directed to presenting all medication orders, infusion and otherwise, including oral medications, at an infusion controller at the point of care of the patient.

In further aspects, there is provided a system for managing pending medication orders pertaining to a patient located in a healthcare facility, the system comprising an infusion pump located at the patient, a controller located at the infusion pump and being in operational control over the infusion pump, the controller comprising a controller processor, a display located at the controller and being under the operational control of the controller, and an identification device configured to acquire patient identification data from the patient and provide that patient identification data to the controller wherein the controller processor is configured to: receive the patient identification data from the identification device, provide a patient-identification-received signal based on the patient identification data, receive pending medication orders pertaining to the identified patient, and display the received pending medication orders for the identified patient on the display.

In more detailed aspects, the identification device is also configured to acquire clinician identification data from a clinician and provide that clinician identification data to the controller and the controller processor is configured to provide a patient-identification-received signal only after it has received the clinician identification data. The identification device is also configured to acquire clinician identification data from a clinician and provide that clinician identification data to the controller, the controller includes a selection device configured to enable selection of a pending medication order displayed on the display, and the controller processor is further configured to receive the clinician identification data and to enable the use of the selection device only after it has received the clinician identification data. The identification device is also configured to acquire clinician identification data from a clinician and provide that clinician identification data to the controller and the controller processor is configured to receive the clinician identification data and to display pending medication orders for the identified patient only if the identified clinician is authorized to assist the identified patient. The identification device is also configured to acquire clinician identification data from a clinician and provide that clinician identification data to the controller, and wherein the controller processor is configured to receive the clinician identification data and to allow a clinician to select a pending order from the displayed pending medication orders only if the identified clinician is authorized to perform the selected pending order.

In further more detailed aspects, the controller processor is configured to provide a pending-order-executed signal to a second processor of the healthcare facility upon a selection of a displayed pending order. The controller processor is configured to provide the pending-order-executed signal to the second processor of the healthcare facility upon manual selection of a displayed pending order. The identification device is also configured to acquire medication identification data from a medication and provide that medication identification data to the controller and the controller processor is configured to automatically select a displayed pending order upon receipt of the medication identification data that corresponds to data of a displayed pending order.

In other aspects, the controller processor is configured to monitor the infusion pump and provide a pending-order-executed signal to a second processor of the healthcare facility upon determining the existence of infusion by the infusion pump in accordance with a displayed pending order. The controller processor is configured to receive a manual indication that a medication has been administered to the patient in accordance with a selected pending medication order and provide a pending-order-executed signal to a second processor of the healthcare facility upon receiving the manual indication of dispensing.

Other aspects pertain to managing controlled items. Upon a selection of a displayed pending order comprising a controlled item, the controller processor provides a controlled-item-administration signal to a second processor of the healthcare facility. The second processor is configured to note the controlled-item-administration signal to a log and thereby resolve a controlled-item-removed transaction. A dispensing processor of a medication dispensing site is configured to provide a controlled-item-removed signal to a second processor of the healthcare facility when a controlled item has been dispensed wherein the second processor monitors time that elapses since provision of the controlled-item-removed signal and if the second processor does not receive a controlled-item-administration signal within a predetermined period of time, the second processor generates an alert signal. The dispensing processor is configured also to send an identification of a pending order that is associated with the controlled item that was removed and identification of a patient for the pending order to the second processor, the second processor determines whether a patient-identification-received signal for the patient of the identified pending order by the dispensing processor has been received and if the patient identification has been received from a controller, the second processor communicates the alert to the controller that provided the patient-identification-received signal. The controller processor is configured to provide the controlled-item-administration signal to the second processor upon manual selection of a displayed pending order. The identification device is also configured to acquire medication identification data from a medication and provide that medication identification data to the controller; and the controller processor is configured to provide the controlled-item-administration signal to the second processor automatically upon receipt of the medication identification data from the identification device that matches a displayed pending order.

In yet other detailed aspects, the identification device is also configured to acquire medication identification data from a medication and provide that medication identification data to the controller, the medication identification data including a drug identifier and drug administration information; and the controller processor compares the drug identifier and drug administration information to the pending medication orders and if a match to a pending order is determined, the controller processor enables selection of the matched pending order. The controller processor automatically programs the infusion pump with pumping parameters for the matched pending order when the matched order is selected. The identification device is also configured to acquire medication identification data from a medication and provide that identification data to the controller, the medication identification data including a drug identifier and drug administration information, and the controller processor is further configured to access a drug library, compare the medication identification data to data of the drug library and provide an alert if the medication identification data is not in conformance with the drug library. Upon selection of a pending medication order, the controller processor communicates to a second processor of the healthcare facility to obtain any updated information about the selected pending medication order.

There is provided a method of providing pending medication orders comprising associating a controller that is located at an infusion pump and in operational control over the infusion pump with a patient by reading identification data from the patient, receiving pending medication orders for the identified patient, displaying received pending medication orders for the identified patient on a display screen located at the controller, and selecting a displayed pending medication order from the controller, the selected pending medication order being selected from among the displayed pending medication orders. In further detail, the method further comprises reading medication identification data from a medication, comparing the read medication data to the displayed pending orders, and selecting a pending order that matches the read medication data. The method further comprises programming the infusion pump upon matching the read medication data with a particular pending order from among the displayed pending medication orders.

In other aspects, there is provided a system for managing pending medication orders pertaining to a patient located in a healthcare facility, the system comprising an infusion pump located at the patient, a controller located at the infusion pump and being in operational control over the infusion pump, the controller comprising a controller processor, a display located at the controller and being under the operational control of the controller, and an identification device configured to acquire patient identification data from the patient and provide that patient identification data to the controller and acquire medication identification data from a medication and provide that medication identification data to the controller, wherein the controller processor is configured to: receive the patient identification data from the identification device, provide a patient-identification-received signal based on the patient identification data, receive pending medication orders pertaining to the identified patient, display the received pending medication orders for the identified patient on the display, automatically select a displayed pending order upon receipt of the medication identification data that corresponds to data of a displayed pending order, and automatically program the infusion pump with pumping parameters for the matched pending order when the matched order is selected.

These and other features and advantages of the present invention will become apparent from the following detailed description of the preferred embodiments which, taken in conjunction with the accompanying drawings, illustrate by way of example the principles of the invention.

DETAILED DESCRIPTION OF THE PREFERRED EMBODIMENTS

Figure 1:
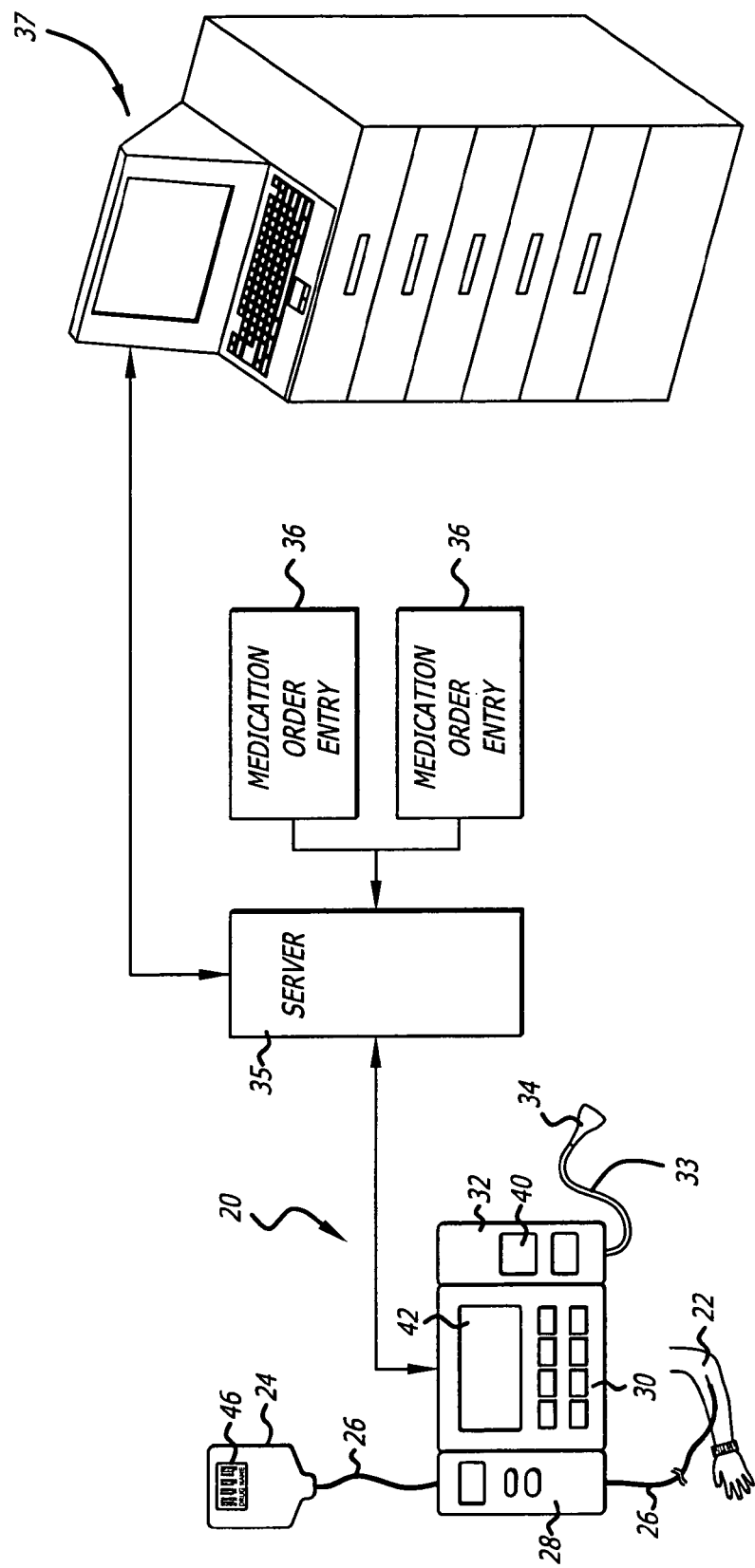
FIG. 1 is a partial block diagram of a system in accordance with aspects of the invention in which an infusion device and associated controller are connected to a health-care facility server that communicates pending medication orders pertaining to a patient upon identification of the patient by the infusion pump or controller, and also shows the interaction of an automated dispensing machine with the server.

Referring now in more detail to the drawings for purposes of illustration of embodiments of the invention, wherein like reference numerals designate corresponding or like elements among the several views, there is shown in FIG. 1 a partial block diagram of a system in accordance with certain aspects of the invention. An infusion pump system 20 is shown connected with a patient 22 to infuse medication fluid from an IV fluid container 24, such as a bag, to the patient through a fluid administration set 26. The pump system includes an infusion pump 28 located at the left side of a controller 30 and an auto identification module 32 or "auto ID module" located to the right side of the controller. The identification module in this case includes a tethered 33 bar code reader 34.

The controller 30 is connected with a server 35, which may take the form of any server or servers in a health care facility. The box 35 identified as "server" may be a single server or it may comprise multiple servers or computers and memory for data storage. The data comprises patient identification data as well as pending medication orders for patients admitted to the health care facility. It may also store clinician identification data and other data. The "server" identified by numeral 35 may also include, for purposes of convenience of discussion and illustration, a server of the company that provides the infusion pump system 20 and establishes communication protocols between that infusion pump system and health care facility servers. The server 35 electronically receives medication orders from physicians from one or more sources 36, such as the pharmacy information system (PIS), laptop computers, physician order entry devices, personal digital assistants ("PDA"), and other devices. Medication orders may also be entered into the server by the pharmacy. The controller 30 may be in communication with the server 35 by any wired or wireless means and the server may be in communication with other devices by wired or wireless means.

As is well known, the pharmacy of the health care facility, or other pharmacy or other department, may print physical labels for the medications to be administered to patients. These labels may include various data such as patient name, medication name, concentration, and may include actual pumping parameters, such as a rate and a volume to be infused ("VTBI") as well as time for administration and other information. The label may also include a bar code label, either two dimensional or linear, or an RFID tag, or other machine readable data source. The labeled medications are transported to the location of the patient or near the patient for administration.

An automated dispensing machine ("ADM") 37 is also shown and typically includes medications for the patients in the vicinity. The ADM has a processor, termed a dispensing processor 50 (shown in FIG. 5), and may require clinician identification before permitting any medications to be withdrawn. The dispensing processor may permit only certain clinicians to remove certain items from the ADM. The ADM may also contain "controlled items" which, for the purposes herein, may be any item desired to be tracked by the healthcare facility in which the ADM is located. This may include narcotics but also may include items of much less sensitivity. When a controlled item is removed from the ADM, the dispensing processor of the ADM may send a controlled-item-removed signal to the server 35 that opens a controlled item transaction. The ADM may also provide the pending order to the server which will include a patient identification. The server may also begin monitoring the amount of time elapsed since the controlled-item-removed signal and if the elapsed time exceeds a predetermined time, send an alert signal. This alert signal may be provided to various locations as determined by the healthcare facility. Such locations may include the pharmacy and administrative offices if a narcotic is involved. Additionally in the case where a patient 22 has been identified to a controller 30, and the patient-identification-received signal provided to the server, the server may compare the patient identification from the controller with the patient associated with the controlled-item-removed signal and correlate the controller to the controlled item transaction. The server may then notify the controller of the alert.

Figure 2:
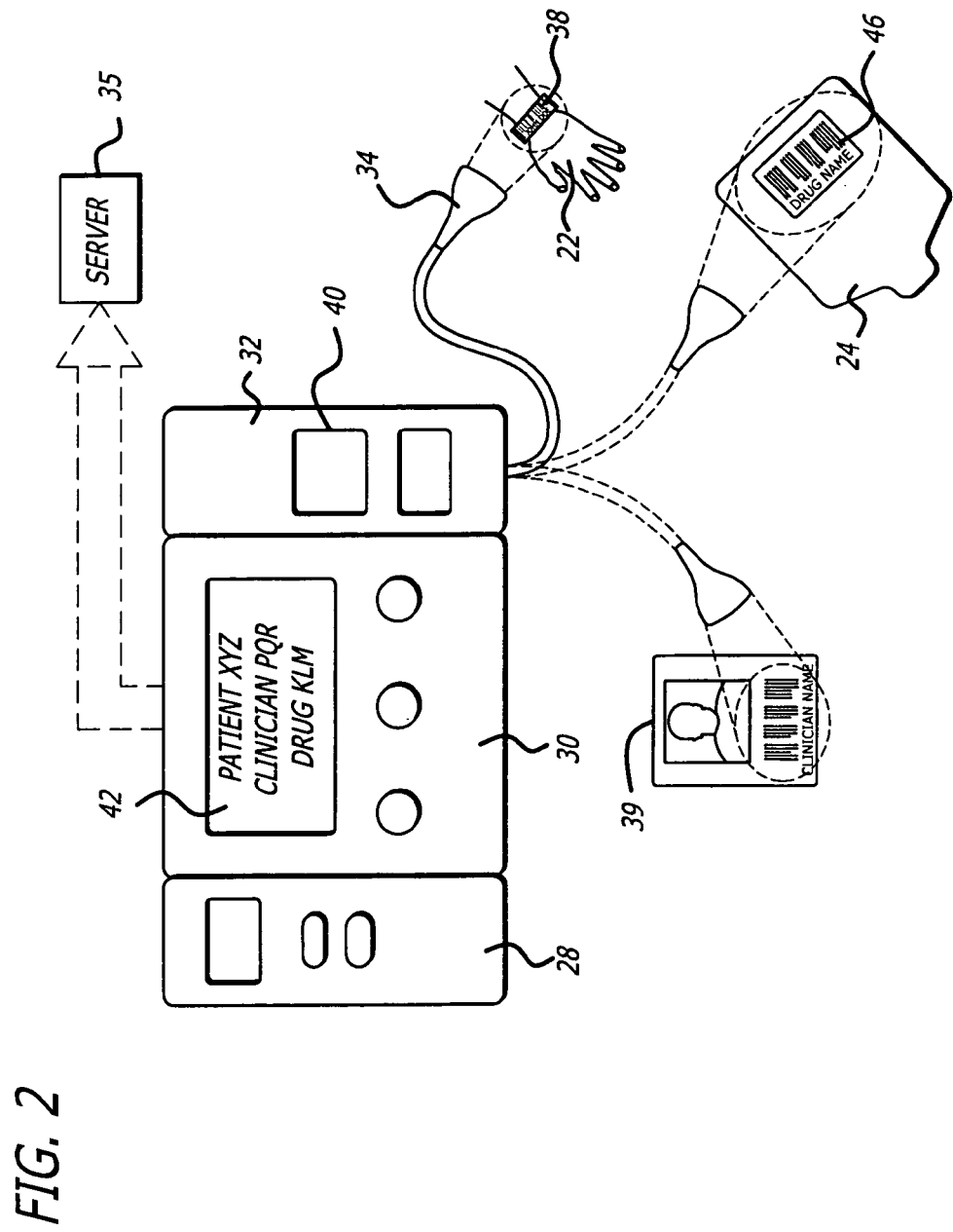
FIG. 2 is a diagram showing a means of identifying a patient, clinician, and medication through the use of an auto identification module connected to a controller associated with the infusion pump of FIG. 1.

Upon initial power up of the controller 30 in this embodiment, the controller prompts the clinician to associate the controller with a patient 22 through use of a patient identification number, or by other means. In the case of FIG. 2, a patient 22 has a wrist band 38 with a line bar code that indicates the patient identification number and/or name, or other information specific to this patient. Using either an embedded bar code reader 40 or a tethered 33 bar code scanner 34 forming a part of an Auto ID module 32 as shown in FIG. 2, the clinician would scan the patient ID bracelet. The scanned patient ID would be sent from the Auto ID module 32 to the controller thereby informing the controller that it is now associated with a particular patient. The auto ID module may communicate by wired or wireless means with the controller. In one case, the controller includes a communications interface ("CI Board") containing a processor, programming, and a substantial memory. The CI Board is in contact with the auto ID module and upon receiving a patient identification, the CI Board then sends a message to the controller telling it that it is now associated with the scanned patient ID. In another embodiment, the functions of the CI Board are all performed by the controller processor 46 (shown in FIG. 5) and other components within the controller itself.

In another embodiment, the clinician would need to scan his/her identification 39 by the method described above to be able to receive even a display of pending medication orders for the patient. In order to do so, the clinician must have been authorized to assist this particular patient. If such authorization has been given, then the pending medication orders for the patient will be displayed on the display 42 at the controller. In another embodiment, the scanned clinician will not be able to select any pending order for the patient unless the clinician has been authorized to assist the identified patient for that particular medication order. For example, some clinicians may be authorized to administer oral medications but not administer infusions. If the clinician is authorized to administer infusions, then in one embodiment, the controller 30 would then make available the drug programming features to the clinician for programming the infusion pump 28.

As used herein, the term "medication" is meant to be understood in a broad sense as pertaining to medical care. "Medication" would include oral medications and infusions of medications, but is also meant to include physical therapy, taking vital signs, preparation for surgery, and other medical care. Also, "administer" is meant to be understood in a broad sense as providing medical care. "Administer" is meant to cover the dispensing of medications, such as oral medications, as well as performing infusions on a patient and other provisions of medical care. The illustrative controller 30 discussed herein and shown in the drawings as a separate unit may actually be a part of an infusion pump or other medical instrument, as may the display 42. The order of identifying individuals or medications or performing steps is provided as embodiments. The identifications may be performed in different orders in certain healthcare facilities, the orders presented here are embodiments.

If authorized, the clinician may then scan a medication container 24 label 46 (FIG. 1) that contains patient ID, drug name, drug concentration, and drug dose. This information would then be passed to the controller where the controller 30 processor 46 would:
1) check to see if the scanned label contains the same patient ID that is associated with the controller to ensure "right" patient;
2) automatically select the drug library entry for the scanned medication to ensure "right" drug and concentration; and
3) automatically populate drug dose parameters in an associated infusion pump to administer the medication to the patient, ensuring "right" dose.

At this point error messages would be displayed to the clinician on the display 42 of the controller 30 if the patient ID in the controller and on the medication label do not match and if the medication scanned is not in the drug library profile that the controller is associated with. As used herein, medication "label" is meant to be understood in a broad sense. Medications may be in containers having labels, but medications may also be provided in individual form and may be scanned for identification.

If all the scanned parameters are valid, the programming parameters are automatically sent to the pump channel that the clinician selects; i.e., the pump channel is automatically programmed for infusion operation. The clinician must manually confirm that these parameters are correct before pumping may be started. In a networked environment, these parameters could be checked with an order entry system to verify that the right order is being administered to the right patient. In another embodiment, the clinician may manually program the pump with the pumping parameters contained in a pending medication order. In one embodiment, selecting a pending order on the display will result in the controller providing further detail of the pending order. Such further detail may contain pumping parameters that may be manually programmed into the pump.

A medication order is entered in the pharmacy and is sent via an electronic interface to a server capable of communication with the controller 30, such as the Pyxis® Profiles Application or an ALARIS server. Such capabilities are provided by Pyxis Products and ALARIS Products respectively of Cardinal Health, San Diego, Calif. At the same time a bar coded IV label is generated in the pharmacy. The bar code contains a patient identification (Patient ID) and a pending order identification (Order ID). Optional information on the bar code is Drug ID and concentration. Once a clinician identifies a patient 22 with an infusion pump 28, the Order ID and drug ID and concentration are sent to the infusion pump or associated controller 30.

Figure 3:
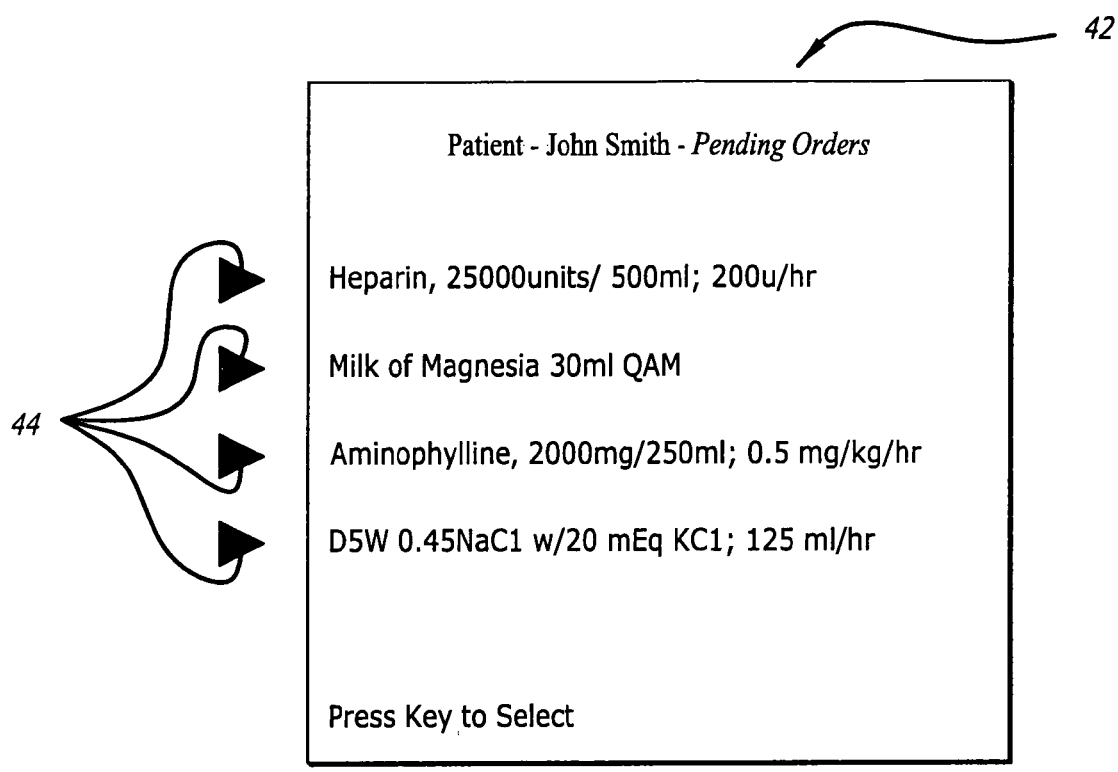
FIG. 3 is an exemplary display of pending medication orders pertaining to an identified patient presented on the display of an infusion pump or associated controller, both of which are located at the point of care of the patient.
Figure 4:
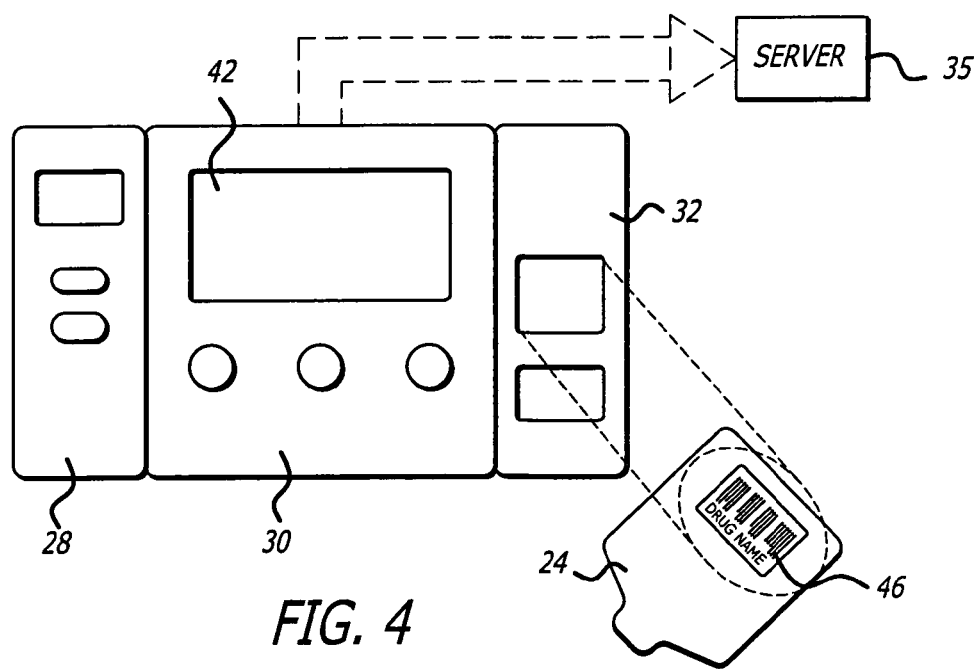
FIG. 4 is a diagram showing a means of identifying a medication through the use of an embedded scanner mounted in an auto identification module connected to a controller associated with the infusion pump of FIG. 1.
Figure 5:
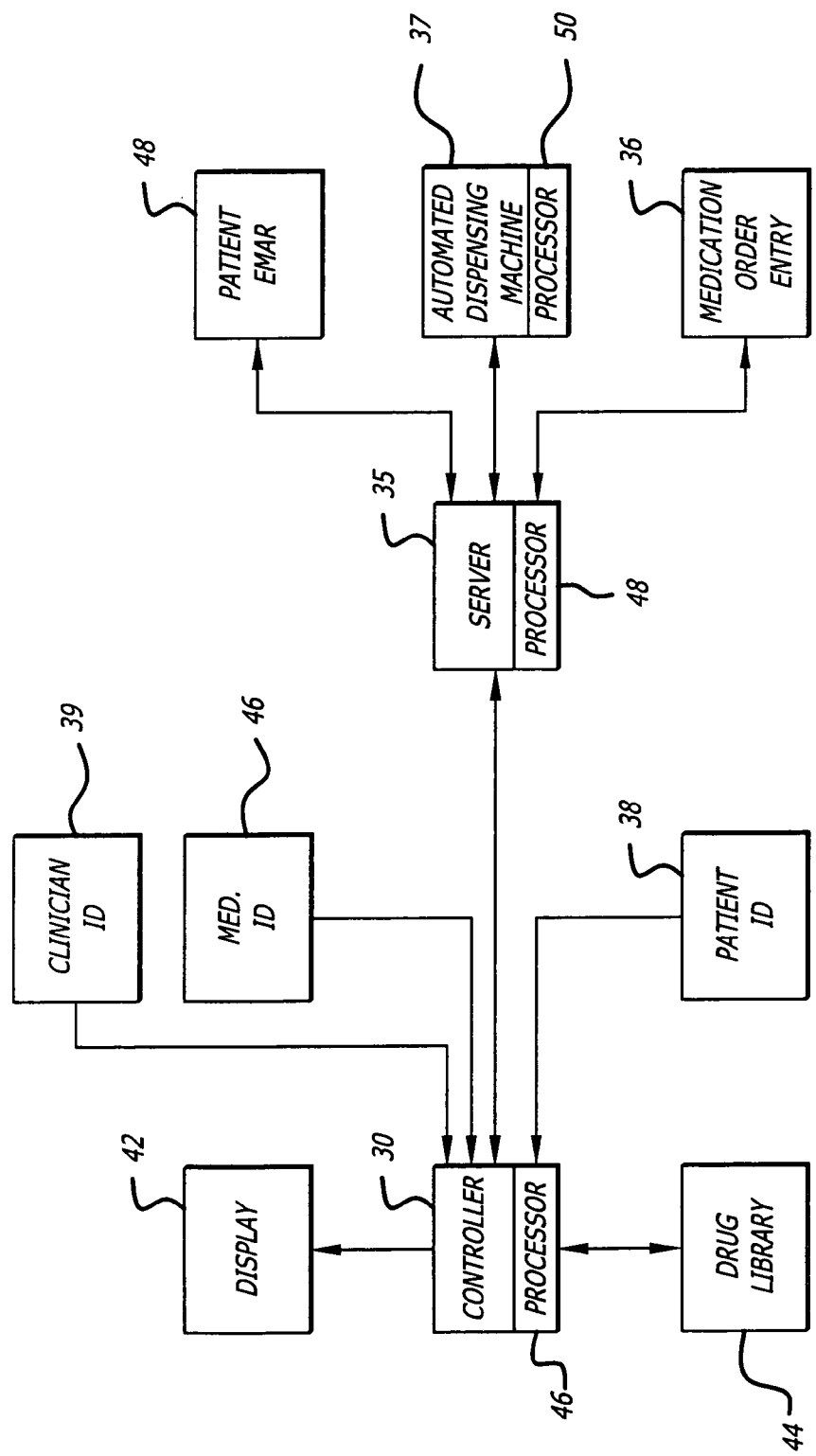
FIG. 5 is a bock diagram showing the interaction of the controller with the display, a drug library, a patient identification device, a medication identification device, a clinician identification device, and a server, in which the server interacts with a medication order entry device or devices, the patient's medical administration record ("MAR"), in this case an eMAR (electronic MAR), and an automated dispensing machine ("ADM"), and also showing the processors of the various devices.

The clinician powers on the controller 30, identifies herself/himself as required, and uses the auto ID module 32 to associate the controller with a patient 22, as shown and discussed above. The controller notifies the server 35 that it has a Patient ID and the server then uploads the pending orders to the controller. The list of pending orders may appear on the display 42 of the controller as shown in FIG. 3. The clinician may select any of the orders by pressing a soft key 44 located adjacent the order listing. The clinician scans the bar code 46 on the IV container 24 as shown in FIG. 4, and can then manually program the infusion. In this embodiment, the scanning was done with an embedded bar code reader 40 located in the front panel of the Auto ID module 32, which is connected to the controller 30. Once the infusion has been manually programmed and started, the infusion data along with Patient ID, Clinician ID, and Order ID are sent by wired means or wireless means back to the server 35, which passes this data through the hospital information system ("HIS") 47 to the patient's eMAR 48, as shown in FIG. 5.

In another embodiment, the clinician need not manually select a pending medication order from the display 42 but may simply scan the medication 24 identification 46 into the controller 30. The controller will then correlate the information from the scanned medication to the list of pending medication orders and upon finding one that corresponds, will select that pending order automatically.

There is also a dynamic update feature. When the clinician scans the patient ID 38 into the controller 30, the controller processor communicates the Patient ID to the server 35 processor. The server processor then communicates all pending medication orders for that identified patient to the controller. These communicated orders may have exactly the same information in them that is on the bar code label 46 on the medication container 24 for the patient, or the order may have been updated since the bar code label was printed. This allows the physician to update the order to reflect changing patient needs even though the barcode label has already been printed and placed on the medication. The barcode on the bag therefore serves primarily to identify the medication to be given, while the server-supplied information has priority over the barcode label as to how the medication is administered to the patient. Physician-initiated changes may also include canceling the order so that the medication is not ever given to the patient.

The management of pending medication orders invention permits the same data that was printed on the bar code label 46 of the medication container 24 to be transmitted to the controller 30 once it has been associated with a patient 22. When a pending medication order set with pending Order IDs, Patient ID, and Drug IDs have been sent to the controller using the management of pending medication orders invention, then when an IV container with that drug or order ID is scanned, the controller can correlate that to the pending order. This is a workflow benefit for nursing and makes updating the eMAR easier.

In a further feature, scanning the data label 46 on the medication container 24 to obtain the medication name may automatically program the infusion pump 28. If the scanned medication matches with a pending order already at the controller, the controller will automatically program the infusion pump for operation in accordance with the physician's order. The clinician need then only check that the programming is in place and is acceptable, check for any drug library limit-exceeded alerts and if none the clinician may press START on the infusion pump to begin the patient's infusion of the medication.

Regardless of how the infusion pump 28 is programmed, the controller 30 may also compare the programmed information to an internal or external drug library 44 having institution-determined safe delivery limits for authorized medications. If the programming is outside a limit, an alert or warning is provided to the clinician. Other action may also be taken. For further details on such drug libraries, see U.S. Pat. Nos. 5,681,285 and 6,269,340 to Ford, incorporated herein by reference.

Figure 6:
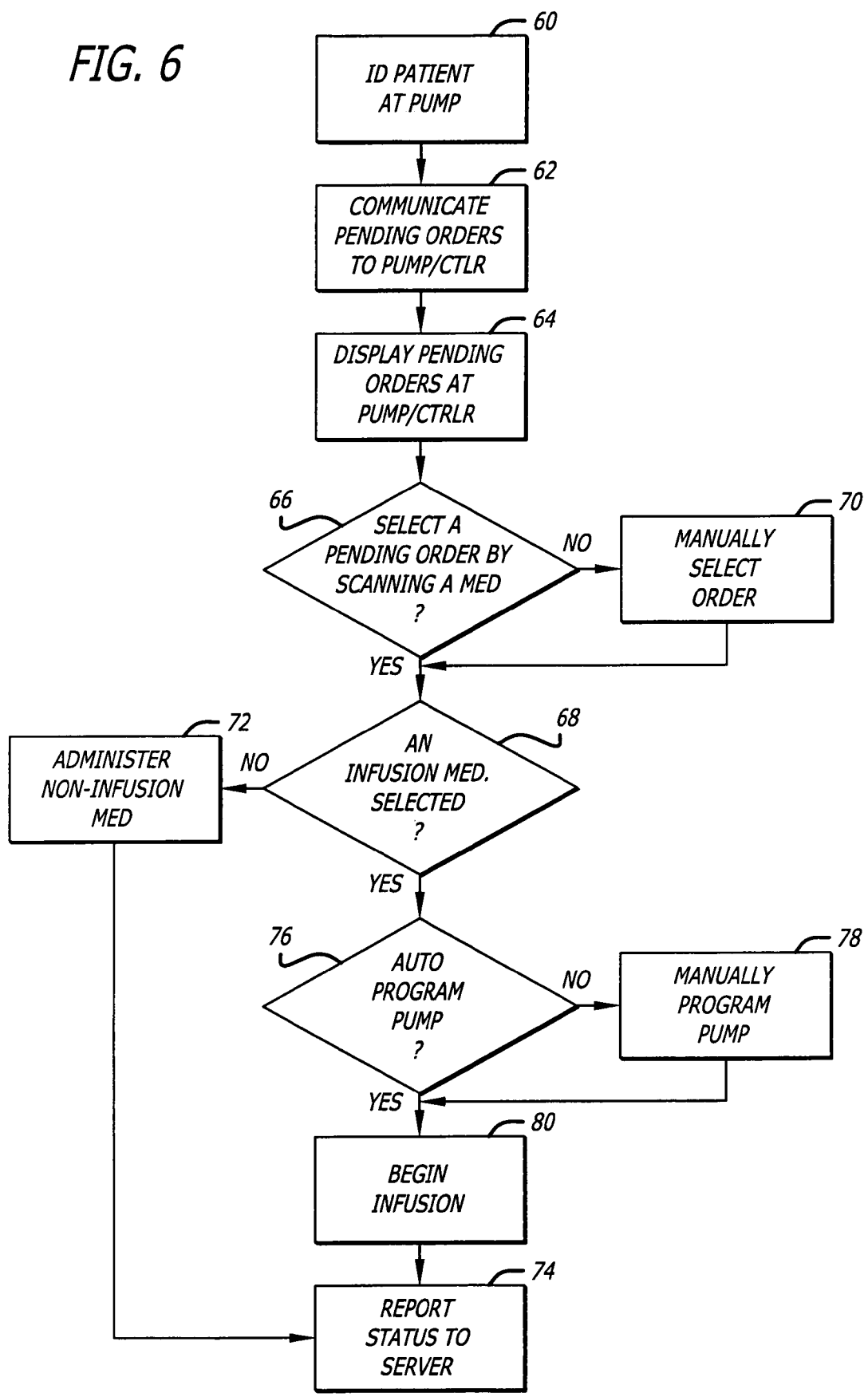
FIG. 6 is a workflow diagram of a method implementing the patient identification and management of pending orders system and method described above, showing administration of infusion and non-infusion medication and reporting of administration status to the server.

Referring to FIG. 6, a workflow diagram is presented and describes an embodiment of a method in accordance with aspects of the management of pending medication orders invention. A patient is identified 60 and the pending orders for that patient are communicated to the infusion pump or controller of that pump 62. The pending orders are displayed at the pump or controller for review by the clinician 64. The clinician may then scan a medication label of a container and if the controller is able to automatically select a pending order based on that medication scan 66, a determination is made as to whether the medication is an infusion, oral, or other 68. If the controller is unable to automatically select a pending order based on a medication container scan, a pending order may be manually selected 70. If the medication is a non-infusion medication, it is administered 72 and a report is sent to the healthcare server 74.

If the medication is administered through an infusion, the controller may automatically program the pump for the infusion parameters 76. If this is not possible, the infusion pump must be manually programmed 78. Infusion now begins 80 by pressing the START button on the pump. A report is sent to the server 74.

In yet a further feature, labeled medications are transported to and stored in computer controlled storage cabinets, referred to herein as automated dispensing machines (ADMs) 37, in the vicinity of the patients for which they are to be administered (see FIG. 1). When the prescribed time comes for a medication to be administered, a clinician logs onto the ADM processor 50 (FIG. 5) and, if the clinician is recognized by the ADM as having the appropriate authority, the clinician is allowed to input the necessary information, such as a patient and medication identifier, in order to remove a selected medication for administration to a selected patient. At such time, the selected medication is designated by the server 35 as being checked out to the clinician. As shown in FIGS. 1 and 5, the ADM is in electronic communication with the server so that activity or transactions at the ADM, such as storage and removal of medication, can be reported to the server. For instance, when a medication is removed, the server obtains information as to the Drug ID of the removed medication, the identity of the clinician who removed it (Clinician ID), the time it was removed, and the Patient ID of the selected patient for whom it is prescribed.

Another feature in accordance with aspects of the invention is that the list of pending medication orders that are shown on the display 42 of the controller 30 also include oral and other types of non-infusion medications in addition to infusion medications. In this way, after a clinician has removed a non-infusion medication, such as an analgesic tablet, from the ADM 37 for administration to the patient associated 22 with the controller 30, the clinician may select a pending medication order to report that the non-infusion medication has been administered. This selection of the pending medication order can be made manually from a selection device, such as softkey 44 on the controller display 42 immediately after administering the non-infusion medication to the patient. In so doing, a communication device of the controller, such as the controller communications interface (CI) board, transmits a signal representative of administration of the non-infusion medication to the server 35. At such time, the transaction of removing the non-infusion medication from the ADM is resolved by the server. If after a preselected period of time the server receives no such signal representative of administration, the server sends an alert or warning to a preselected individual or individuals, such as another clinician, a supervisor, or administrator, to resolve the transaction or investigate the delay in administration.

In other cases, an infusion or non-infusion medication 24 removed from the ADM 37 may have a bar code 46, radio frequency identification (RFID) tag, or other means of identification on it or associated with it. In these cases, the transaction associated with removal of the medication from the ADM is resolved upon an indication that the removed medication was administered to the right patient 22. The infusion pump system 20 can provide this indication of administration of the medication to the right patient to the server 35 in many ways, such as for example when the clinician (1) scans the bar code or RFID tag of the medication with a data reader 34, such as the Auto-ID module 32, (2) manually selects 44 a corresponding medication order on the list of displayed 42 pending medication orders on the controller 30, and (3) manually inputs the Drug ID of the medication into the user interface of the controller.

In a still further feature as discussed briefly above, the server 35 stores data regarding the movement and use of controlled items. This allows an institution to track the movement and use of controlled items, which may, for example, be performed to satisfy regulatory requirements or to facilitate internal workflow or auditing studies. Controlled items typically include certain narcotics and other so-called "controlled substances," but may also include any item an institution wishes to track. It is to be understood that a controlled item need not be a medication and may be a device, such as an empty syringe, for example. With this feature, the server 35 keeps a medication transaction log that may include the time, Clinician ID, Patient ID, Drug ID, and other information associated with the movement and use of a controlled item. With such information, institutions may, for example, ascertain whether removal of certain controlled items tend to have a greater than average resolution time or tend to get lost, or whether certain clinicians have a tendency to lose or delay administration of particular controlled items.

Another feature is that the controller 30 keeps a Continuous Quality Improvement (CQI) log of activity on the infusion pump system 20. The log includes, but is not limited to, data involving errors and corrections made in programming the infusion pumps 28. As mentioned above, the controller processor 46 always compares the programmed information, whether obtained from scanning a label on a medication or obtained from manual input by a clinician, to an internal or external drug library 44 having institution-determined safe delivery limits for the medication. If the programming is outside a limit, an alert or warning is generated. Such alerts and warnings, the key-strokes or other actions taken by the clinician leading up to the alert or warning, and the key-strokes or other actions taken by the clinician in response to the alert or warning are stored in the CQI log of the controller. Such data may be used by the institution to support workflow study, auditing, training, and other efforts to improve the delivery of healthcare services.

Figure 7:
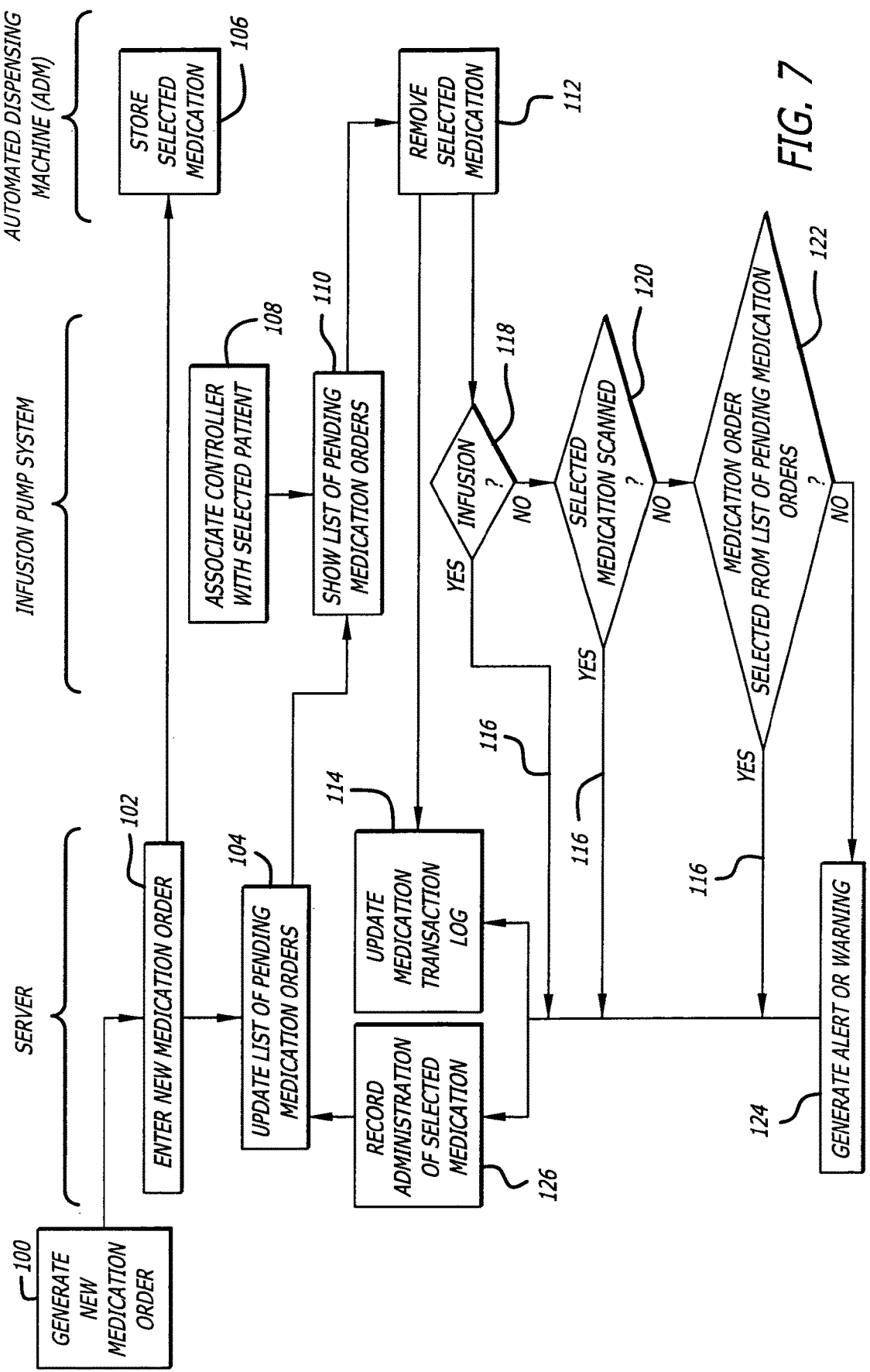
FIG. 7 is a workflow diagram of a method implementing the patient identification and pending medication orders management system described above, showing closed-loop tracking of medications and medication orders.

Referring now to FIG. 7, a workflow diagram is presented and describes an embodiment of a method in accordance with aspects of the management of pending medications orders invention. A new medication order is generated 100 by a physician to have a selected medication administered to a selected patient. The medication order need not involve a drug medication, such as for example an order to provide a certain type of food or to take and report the vital signs of a patient. When the medication order involves a drug medication, the new medication order is communicated to a pharmacy, which enters 102 the new medication order into the server. At such time, the server updates 104 a list of pending medication orders for the selected patient to include the new medication order having an assigned Order ID. The pharmacy also instructs a technician to transport the selected medication, now associated with the Order ID, from the pharmacy and to store 106 it in an ADM 37 (FIG. 1) located in the general vicinity of the selected patient.

A clinician accesses a controller 30 of an infusion pump system 20 by scanning the clinician identification 39 from his or her identification device, such as a card or badge 37 (FIG. 2), and associates 108 the controller with the selected patient 22 by scanning the patient's identification device 38, such as the patient's bracelet (FIG. 2) for example. Thereafter, the controller provides a patient-identification received signal to the server 35, which responds by sending pending medication orders for the identified patient. At such time, the controller display screen 42 (FIG. 3) of the infusion pump system displays 110 the list of pending medication orders for the selected patient. The displayed pending medication orders may be updated dynamically whenever another medication order is generated or an existing medication order is cancelled or modified for the selected patient in accordance with certain aspects.

Upon seeing the new medication order among the pending medication orders on the controller display, the clinician obtains the selected medication from a medication dispensing site, such as a pharmacy or an automated dispensing machine ("ADM"). In cases where the selected medication is stored in an ADM, the clinician logs into the ADM and removes 112 the selected medication from the ADM. At such time, the ADM communicates with the server 35, which updates 114 a medication tracking log to reflect that the selected medication was removed from the ADM, and may include other information as desired. As previously mentioned, the medication transaction log is useful in tracking movement and use of controlled items, such as narcotic medications that may be regulated by government agencies.

Upon a positive indication 116 from the infusion pump system of the administration of the medication, the server updates 104 the medication transaction log to reflect that the selected medication was administered to the selected patient. When infusion of the selected medication is started 118, the status of administration is dynamically reported by the infusion pump system controller to the server, ultimately resolving the removal transaction of the selected medication from the ADM. In cases when the selected medication is a non-infusion medication, resolution of its removal from the ADM occurs automatically when its bar code, RFID, or other machine readable tag is scanned 120 with the infusion pump system Auto-ID module 32 or when a medication order is manually selected 122 at the infusion pump system 20 controller 30.

When no positive indication from the infusion pump system 20 is received by the server 35 after a predetermined period of time after the selected medication was removed from the ADM 37, the server may generate 124 an alert or warning in order to prompt the clinician or some other person to investigate the delay in administration. This may be done in all cases where the medication or medical device is considered of significant importance to be tracked as a controlled item. The server updates 114 the medication transaction log to reflect resolution of the alert or warning, which may occur by returning the medication to the ADM, reporting that the medication was wasted, or by other means. In this way, the management of pending medication orders of the present invention allows for efficient closed-loop tracking of medications to ensure that they are administered to the right patient at the right time and the right manner.

As previously mentioned, when a label 46 or tag on a medication or medication container 24 is scanned by the Auto-ID module 32, the controller 30 processor 46 can automatically correlate the medication to a particular pending medication order from among the pending medication orders obtained from the server 35. After this selection of a medication order is communicated to the server, the server records 126 that the selected medication order has been performed and updates 104 the list of pending medication orders to prevent it from being inadvertently performed again. Thus, it will be appreciated that the management of pending medications order system and method of the present invention allows for efficient closed-loop tracking of medication orders, whether or not they involve medications, to ensure that they are performed properly.

While particular forms of the invention have been illustrated and described, it will also be apparent to those skilled in the art that various modifications can be made without departing from the scope of the invention. Accordingly, it is not intended that the invention be limited except by the appended claims.

What is claimed is:

1. A system for managing pending medication orders pertaining to a patient located in a healthcare facility, the system comprising:
    an infusion pump;
    a controller located at the infusion pump and being in operational control over the infusion pump, the controller comprising a controller processor;
    a display device located at the controller and being under the operational control of the controller; and
    an identification device associated with the controller and configured to acquire identification data from a caregiver or a patient and provide that patient identification data to the controller;
    wherein the controller processor is configured to:
        receive patient identification data from the identification device;
        receive caregiver identification data from the identification device;
        receive, based on the patient identification data, pending medication orders pertaining to a patient identified by the patient identification data;
        determine, responsive to receiving the patient identification data and the caregiver identification data, whether a caregiver identified by the caregiver identification data is authorized to administer medications to the patient identified by the patient identification data; and
        provide for display, for selection on the display device, responsive to and only when determining that the caregiver is authorized to administer medications to the patient, a listing of the pending medication orders pertaining to the identified patient;
        receive a selected medication order from the displayed listing of the pending medication orders; and
        provide, over a network, an indication that an administration of a medication corresponding to the selected medication order has been initiated.

2. The system of claim 1, further comprising:
    a server configured to:
        receive an indication that the medication was removed for the selected medication order from a medication dispensing device;
        determine, based on the indication that the medication was removed from the medication dispensing device, an elapsed time between the medication being removed and a current time; and
        send an alert indication responsive to the elapsed time satisfying a predetermined threshold of time before the indication that the administration has been initiated is received by the server over the network.

3. The system of claim 2, wherein the alert indication is provided by the server to the controller.

4. The system of claim 2, wherein the indication that the medication was removed from the medication dispensing device is received after the listing of the pending medication orders is provided for display but before receiving the indication that the administration has been initiated.

5. The system of claim 2, further comprising:
    a server configured to:
        receive the patient identification data and the caregiver identification data from the controller; and
        provide, based on the patient identification data, the pending medication orders to the controller; and
        generate a transaction log comprising the patient identification data, the caregiver identification data and identification data pertaining to the medication removed from the medication dispensing device.

6. The system of claim 1, wherein the identification device is configured to obtain the patient identification data or the caregiver identification data by way of a scanning action.

7. The system of claim 6, wherein the identification device is a radio frequency identification (RFID) scanner device.

8. The system of claim 6, wherein the selected medication order is received by scanning a label or radio frequency identification (RFID) tag affixed to a medication container associated with the selected medication order.

9. The system of claim 1, wherein the controller is further configured to:
    determine whether the selected medication order is for an infusion medication or a non-infusion medication; and
    automatically program, responsive to determining that the selected medication order is for an infusion medication, the infusion pump with infusion parameters corresponding to the selected medication order.

10. A method for managing pending medication orders pertaining to a patient located in a healthcare facility, the method comprising:
    receiving patient identification data from an identification device associated with an infusion device controller;
    receiving caregiver identification data from the identification device;

obtaining, based on the patient identification data, pending medication orders pertaining to a patient identified by the patient identification data;

determining, responsive to receiving the patient identification data and the caregiver identification data, whether a caregiver identified by the caregiver identification data is authorized to administer medications to the patient identified by the patient identification data; and providing for display, for selection on a display device associated with the infusion device controller, responsive to and only when determining that the caregiver is authorized to administer medications to the patient, a listing of the pending medication orders pertaining to the identified patient;

receiving a selected medication order from the displayed listing of the pending medication orders; and providing, over a network, an indication that an administration of a medication corresponding to the selected medication order has been initiated.

11. The method of claim 10, further comprising:
receiving an indication that the medication was removed for the selected medication order from a medication dispensing device;

determining, based on the indication that the medication was removed from the medication dispensing device, an elapsed time between the medication being removed and a current time; and providing an alert indication responsive to the elapsed time satisfying a predetermined threshold of time before the indication that the administration has been initiated is received.

12. The method of claim 11, wherein the alert indication is provided by a server to the infusion device controller.

13. The method of claim 11, wherein the indication that the medication was removed from the medication dispensing device is received after the listing of the pending medication orders is provided for display but before receiving the indication that the administration has been initiated.

14. The method of claim 11, further comprising:
receiving the patient identification data and the caregiver identification data from the controller; and generating a transaction log comprising the patient identification data, the caregiver identification data and identification data pertaining to the medication removed from the medication dispensing device.

15. The method of claim 10, wherein the identification device is configured to obtain the patient identification data or the caregiver identification data by way of a scanning action.

16. The method of claim 15, wherein the identification device is a radio frequency identification (RFID) scanner device.

17. The method of claim 15, wherein the selected medication order is received by scanning a label or radio frequency identification (RFID) tag affixed to a medication container associated with the selected medication order.

18. The method of claim 10, further comprising:
determining whether the selected medication order is for an infusion medication or a non-infusion medication; and automatically programming, by a processor, responsive to determining that the selected medication order is for an infusion medication, the infusion pump with infusion parameters corresponding to the selected medication order.

19. A non-transitory computer readable medium having instructions thereon that, when executed by one or more computing devices, cause the one or more computing devices to perform operations comprising:
receiving patient identification data from an identification device associated with an infusion device controller;

receiving caregiver identification data from the identification device;

obtaining, based on the patient identification data, pending medication orders pertaining to a patient identified by the patient identification data;

determining, responsive to receiving the patient identification data and the caregiver identification data, whether a caregiver identified by the caregiver identification data is authorized to administer medications to the patient identified by the patient identification data; and providing for display, for selection on a display device associated with the infusion device controller, responsive to and only when determining that the caregiver is authorized to administer medications to the patient, a listing of the pending medication orders pertaining to the identified patient;

receiving a selected medication order from the displayed listing of the pending medication orders; and providing, over a network, an indication that an administration of a medication corresponding to the selected medication order has been initiated.

20. The transitory computer readable medium of claim 19, the operations further comprising:
receiving an indication that the medication was removed for the selected medication order from a medication dispensing device;

determining, based on the indication that the medication was removed from the medication dispensing device, an elapsed time between the medication being removed and a current time; and providing an alert indication responsive to the elapsed time satisfying a predetermined threshold of time before the indication that the administration has been initiated is received.

* * * * *